United States Patent
Chen et al.

(10) Patent No.: US 11,572,548 B2
(45) Date of Patent: Feb. 7, 2023

(54) REACTION MIXTURE FOR SYNTHESIS OF ALPHA1-2-FUCOSIDES

(71) Applicant: The Regents of the University of California, Oakland, CA (US)

(72) Inventors: Xi Chen, Davis, CA (US); Chao Zhao, Fuzhou (CN); Hai Yu, Woodland, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/062,883

(22) PCT Filed: Dec. 19, 2016

(86) PCT No.: PCT/US2016/067601
§ 371 (c)(1),
(2) Date: Jun. 15, 2018

(87) PCT Pub. No.: WO2017/106864
PCT Pub. Date: Jun. 22, 2017

(65) Prior Publication Data
US 2018/0371432 A1    Dec. 27, 2018

Related U.S. Application Data

(60) Provisional application No. 62/269,574, filed on Dec. 18, 2015.

(51) Int. Cl.
| | | |
|---|---|---|
| *C12N 9/10* | (2006.01) |
| *C12P 19/18* | (2006.01) |
| *C12N 15/70* | (2006.01) |
| *C12P 19/26* | (2006.01) |
| *C12P 19/44* | (2006.01) |

(52) U.S. Cl.
CPC ........... *C12N 9/1051* (2013.01); *C12N 15/70* (2013.01); *C12P 19/18* (2013.01); *C12P 19/26* (2013.01); *C12P 19/44* (2013.01); *C12Y 204/01* (2013.01); *C12Y 207/01052* (2013.01)

(58) Field of Classification Search
None
See application file for complete search history.

(56) References Cited

FOREIGN PATENT DOCUMENTS

WO    2015/175801 A1    11/2015

OTHER PUBLICATIONS

International Search Report and Written Opinion in PCT/US2016/067601 dated May 8, 2017; 15 pages.
Baumgartner, F. et al.; "Synthesis of fucosylated lacto-N-tetraose using whole-cell biotransformation"; *Bioorganic and Medicinal Chemistry*; vol. 23, No. 21; Nov. 1, 2015; pp. 6799-6806.
Zhang, L. et al.; "*Helicobacter hepaticus* Hh0072 gene encodes a novel alpha 1-3-fucosyltransferase belonging to CAZy GT11 family"; *Glycobiology*; vol. 20, No. 9; Sep. 2010; pp. 1077-1088.
Harold, F.M.; "Inorganic Polyphosphates in Biology: Structure, Metabolism, and Function"; *Bacteriological Reviews*; vol. 30, No. 4; Dec. 1966; pp. 772-794.
Kotake, T. et al.; "A Bifunctional Enzyme with L-Fucokinase and GDP-L-fucose Pyrophosphorylase Activities Salvages Free L-Fucose in *Arabidopsis*"; *The Journal of Biological Chemistry*; vol. 283, No. 13; Mar. 28, 2008; pp. 8125-8135.

*Primary Examiner* — Hope A Robinson
(74) *Attorney, Agent, or Firm* — Kilpatrick Townsend & Stockton LLP

(57) ABSTRACT

α1-2-fucosyltransferases, and methods and compositions for making and using α1-2-fucosyltransferases, are described herein.

21 Claims, 12 Drawing Sheets
Specification includes a Sequence Listing.

FIG. 1

Galβ1-3GlcNAcβ2AA

Fucα1–2Galβ1–3GalNAcαProN₃ (1)

Fucα1–2Galβ1–3GalNAcβProN₃ (2)

Fucα1–2Galβ1–3GlcNAcαProN₃ (3)

Fucα1–2Galβ1–3GlcNAcβProN₃ (4)

Fucα1–2LNT or LNFP I (5)

SEQUENCE LISTING

<160> NUMBER OF SEQ ID NOS: 19

<210> SEQ ID NO 1
<211> LENGTH: 293
<212> TYPE: PRT
<213> ORGANISM: Thermosynechococcus elongatus

<400> SEQUENCE: 1

```
Met Ile Ile Val His Leu Cys Gly Gly Leu Gly Asn Gln Met Phe Gln
1               5                   10                  15

Tyr Ala Ala Gly Leu Ala Ala Ala His Arg Ile Gly Ser Glu Val Lys
            20                  25                  30

Phe Asp Thr His Trp Phe Asp Ala Thr Cys Leu His Gln Gly Leu Glu
        35                  40                  45

Leu Arg Arg Val Phe Gly Leu Glu Leu Pro Glu Pro Ser Ser Lys Asp
    50                  55                  60

Leu Arg Lys Val Leu Gly Ala Cys Val His Pro Ala Val Arg Arg Leu
65                  70                  75                  80

Leu Ala Gly His Phe Leu His Gly Leu Arg Pro Lys Ser Leu Val Ile
                85                  90                  95

Gln Pro His Phe His Tyr Trp Thr Gly Phe Glu His Leu Pro Asp Asn
            100                 105                 110

Val Tyr Leu Glu Gly Tyr Trp Gln Ser Glu Arg Tyr Phe Ser Asn Ile
        115                 120                 125

Ala Asp Ile Ile Arg Gln Gln Phe Arg Phe Val Glu Pro Leu Asp Pro
    130                 135                 140

His Asn Ala Ala Leu Met Asp Glu Met Gln Ser Gly Val Ser Val Ser
145                 150                 155                 160

Leu His Ile Arg Arg Gly Asp Tyr Phe Asn Asn Pro Gln Met Arg Arg
                165                 170                 175

Val His Gly Val Asp Leu Ser Glu Tyr Tyr Pro Ala Ala Val Ala Thr
            180                 185                 190

Met Ile Glu Lys Thr Asn Ala Glu Arg Phe Tyr Val Phe Ser Asp Asp
        195                 200                 205

Pro Gln Trp Val Leu Glu His Leu Lys Leu Pro Val Ser Tyr Thr Val
    210                 215                 220

Val Asp His Asn Arg Gly Ala Ala Ser Tyr Arg Asp Met Gln Leu Met
225                 230                 235                 240

Ser Ala Cys Arg His His Ile Ile Ala Asn Ser Thr Phe Ser Trp Trp
                245                 250                 255

Gly Ala Trp Leu Asn Pro Arg Pro Asp Lys Val Val Ile Ala Pro Arg
            260                 265                 270

His Trp Phe Asn Val Asp Val Phe Asp Thr Arg Asp Leu Tyr Cys Pro
        275                 280                 285

Gly Trp Ile Val Leu
    290
```

<210> SEQ ID NO 2
<211> LENGTH: 969
<212> TYPE: PRT
<213> ORGANISM: Artificial Sequence
<220> FEATURE:
<223> OTHER INFORMATION: Synthetic construct

<400> SEQUENCE: 2

```
Met Gly Ser Ser His His His His His His Ser Ser Gly Leu Val Pro
1               5                   10                  15

Arg Gly Ser His Met Gln Lys Leu Leu Ser Leu Pro Pro Asn Leu Val
            20                  25                  30

Gln Ser Phe His Glu Leu Glu Arg Val Asn Arg Thr Asp Trp Phe Tyr
        35                  40                  45
```

-continued

```
Thr Ser Asp Pro Val Gly Lys Lys Leu Gly Ser Gly Gly Thr Ser
    50              55              60
Trp Leu Glu Glu Cys Tyr Asn Glu Tyr Ser Asp Gly Ala Thr Phe
65              70              75              80
Gly Glu Trp Leu Glu Lys Glu Lys Arg Ile Leu His Ala Gly Gly
            85              90              95
Gln Ser Arg Arg Leu Pro Gly Tyr Ala Pro Ser Gly Lys Ile Leu Thr
        100             105             110
Pro Val Pro Val Phe Arg Trp Glu Arg Gly Gln His Leu Gly Gln Asn
            115             120             125
Leu Leu Ser Leu Gln Leu Pro Leu Tyr Glu Lys Ile Met Ser Leu Ala
    130             135             140
Pro Asp Lys Leu His Thr Leu Ile Ala Ser Gly Asp Val Tyr Ile Arg
145             150             155             160
Ser Glu Lys Pro Leu Gln Ser Ile Pro Glu Ala Asp Val Val Cys Tyr
                165             170             175
Gly Leu Trp Val Asp Pro Ser Leu Ala Thr His His Gly Val Phe Ala
            180             185             190
Ser Asp Arg Lys His Pro Glu Gln Leu Asp Phe Met Leu Gln Lys Pro
        195             200             205
Ser Leu Ala Glu Leu Glu Ser Leu Ser Lys Thr His Leu Phe Leu Met
    210             215             220
Asp Ile Gly Ile Trp Leu Ser Asp Arg Ala Val Glu Ile Leu Met
225             230             235             240
Lys Arg Ser His Lys Glu Ser Ser Glu Glu Leu Lys Tyr Tyr Asp Leu
                245             250             255
Tyr Ser Asp Phe Gly Leu Ala Leu Gly Thr His Pro Arg Ile Glu Asp
            260             265             270
Glu Glu Val Asn Thr Leu Ser Val Ala Ile Leu Pro Leu Pro Gly Gly
        275             280             285
Glu Phe Tyr His Tyr Gly Thr Ser Lys Glu Leu Ile Ser Ser Thr Leu
    290             295             300
Ser Val Gln Asn Lys Val Tyr Asp Gln Arg Arg Ile Met His Arg Lys
305             310             315             320
Val Lys Pro Asn Pro Ala Met Phe Val Gln Asn Ala Val Arg Ile
                325             330             335
Pro Leu Cys Ala Glu Asn Ala Asp Leu Trp Ile Glu Asn Ser His Ile
            340             345             350
Gly Pro Lys Trp Lys Ile Ala Ser Arg His Ile Ile Thr Gly Val Pro
        355             360             365
Glu Asn Asp Trp Ser Leu Ala Val Pro Ala Gly Val Cys Val Asp Val
    370             375             380
Val Pro Met Gly Asp Lys Gly Phe Val Ala Arg Pro Tyr Gly Leu Asp
385             390             395             400
Asp Val Phe Lys Gly Asp Leu Arg Asp Ser Lys Thr Thr Leu Thr Gly
                405             410             415
Ile Pro Phe Gly Glu Trp Met Ser Lys Arg Gly Leu Ser Tyr Thr Asp
            420             425             430
Leu Lys Gly Arg Thr Asp Asp Leu Gln Ala Val Ser Val Phe Pro Met
        435             440             445
Val Asn Ser Val Glu Glu Leu Gly Leu Val Leu Arg Trp Met Leu Ser
    450             455             460
Glu Pro Glu Leu Glu Glu Gly Lys Asn Ile Trp Leu Arg Ser Glu His
```

```
             465                 470                 475                 480
         Phe Ser Ala Asp Glu Ile Ser Ala Gly Ala Asn Leu Lys Arg Leu Tyr
                         485                 490                 495
         Ala Gln Arg Glu Glu Phe Arg Lys Gly Asn Trp Gln Ala Leu Ala Val
                     500                 505                 510
         Asn His Glu Lys Ser Val Phe Tyr Gln Leu Asp Leu Ala Asp Ala Ala
                     515                 520                 525
         Glu Asp Phe Val Arg Leu Gly Leu Asp Met Pro Glu Leu Leu Pro Glu
                     530                 535                 540
         Asp Ala Leu Gln Met Ser Arg Ile His Asn Arg Met Leu Arg Ala Arg
         545                 550                 555                 560
         Ile Leu Lys Leu Asp Gly Lys Asp Tyr Arg Pro Glu Gln Ala Ala
                         565                 570                 575
         Phe Asp Leu Leu Arg Asp Gly Leu Leu Asp Gly Ile Ser Asn Arg Lys
                         580                 585                 590
         Ser Thr Pro Lys Leu Asp Val Tyr Ser Asp Gln Ile Val Trp Gly Arg
                     595                 600                 605
         Ser Pro Val Arg Ile Asp Met Ala Gly Gly Trp Thr Asp Thr Pro Pro
                 610                 615                 620
         Tyr Ser Leu Tyr Ser Gly Gly Asn Val Val Asn Leu Ala Ile Glu Leu
         625                 630                 635                 640
         Asn Gly Gln Pro Pro Leu Gln Val Tyr Val Lys Pro Cys Lys Asp Phe
                         645                 650                 655
         His Ile Val Leu Arg Ser Ile Asp Met Gly Ala Met Glu Ile Val Ser
                         660                 665                 670
         Thr Phe Asp Glu Leu Gln Asp Tyr Lys Lys Ile Gly Ser Pro Phe Ser
                     675                 680                 685
         Ile Pro Lys Ala Ala Leu Ser Leu Ala Gly Phe Ala Pro Ala Phe Ser
                     690                 695                 700
         Ala Val Ser Tyr Ala Ser Leu Glu Glu Gln Leu Lys Asp Phe Gly Ala
         705                 710                 715                 720
         Gly Ile Glu Val Thr Leu Leu Ala Ala Ile Pro Ala Gly Ser Gly Leu
                         725                 730                 735
         Gly Thr Ser Ser Ile Leu Ala Ser Thr Val Leu Gly Ala Ile Asn Asp
                     740                 745                 750
         Phe Cys Gly Leu Ala Trp Asp Lys Asn Glu Ile Cys Gln Arg Thr Leu
                     755                 760                 765
         Val Leu Glu Gln Leu Leu Thr Thr Gly Gly Trp Gln Asp Gln Tyr
         770                 775                 780
         Gly Gly Val Leu Gln Gly Val Lys Leu Leu Gln Thr Glu Ala Gly Phe
         785                 790                 795                 800
         Ala Gln Ser Pro Leu Val Arg Trp Leu Pro Asp His Leu Phe Thr His
                     805                 810                 815
         Pro Glu Tyr Lys Asp Cys His Leu Leu Tyr Tyr Thr Gly Ile Thr Arg
                     820                 825                 830
         Thr Ala Lys Gly Ile Leu Ala Glu Ile Val Ser Ser Met Phe Leu Asn
                     835                 840                 845
         Ser Ser Leu His Leu Asn Leu Leu Ser Glu Met Lys Ala His Ala Leu
                     850                 855                 860
         Asp Met Asn Glu Ala Ile Gln Arg Gly Ser Phe Val Glu Phe Gly Arg
         865                 870                 875                 880
         Leu Val Gly Lys Thr Trp Glu Gln Asn Lys Ala Leu Asp Ser Gly Thr
                         885                 890                 895
```

Asn Pro Pro Ala Val Glu Ala Ile Ile Asp Leu Ile Lys Asp Tyr Thr
                900                 905                 910

Leu Gly Tyr Lys Leu Pro Gly Ala Gly Gly Gly Tyr Leu Tyr Met
        915                 920                 925

Val Ala Lys Asp Pro Gln Ala Val Arg Ile Arg Lys Ile Leu Thr
    930                 935                 940

Glu Asn Ala Pro Asn Pro Arg Ala Arg Phe Val Glu Met Thr Leu Ser
945                 950                 955                 960

Asp Lys Gly Phe Gln Val Ser Arg Ser
                965

<210> SEQ ID NO 3
<211> LENGTH: 183
<212> TYPE: PRT
<213> ORGANISM: Artificial Sequence
<220> FEATURE:
<223> OTHER INFORMATION: Synthetic construct

<400> SEQUENCE: 3

Met Gly Leu Glu Thr Val Pro Ala Gly Lys Ala Leu Pro Asp Asp Ile
1               5                   10                  15

Tyr Val Val Ile Glu Ile Pro Ala Asn Ser Asp Pro Ile Lys Tyr Glu
            20                  25                  30

Val Asp Lys Glu Ser Gly Ala Leu Phe Val Asp Arg Phe Met Ala Thr
        35                  40                  45

Ala Met Phe Tyr Pro Ala Asn Tyr Gly Tyr Val Asn Asn Thr Leu Ser
    50                  55                  60

Leu Asp Gly Asp Pro Val Asp Val Leu Val Pro Thr Pro Tyr Pro Leu
65                  70                  75                  80

Gln Pro Gly Ser Val Ile Arg Cys Arg Pro Val Gly Val Leu Lys Met
                85                  90                  95

Thr Asp Glu Ala Gly Ser Asp Ala Lys Val Val Ala Val Pro His Ser
            100                 105                 110

Lys Leu Thr Lys Glu Tyr Asp His Ile Lys Asp Val Asn Asp Leu Pro
        115                 120                 125

Ala Leu Leu Lys Ala Gln Ile Gln His Phe Phe Glu Ser Tyr Lys Ala
    130                 135                 140

Leu Glu Ala Gly Lys Trp Val Lys Val Asp Gly Trp Glu Gly Val Asp
145                 150                 155                 160

Ala Ala Arg Gln Glu Ile Leu Asp Ser Phe Glu Arg Ala Lys Lys Leu
                165                 170                 175

Glu His His His His His His
            180

<210> SEQ ID NO 4
<211> LENGTH: 2910
<212> TYPE: DNA
<213> ORGANISM: Artificial Sequence
<220> FEATURE:
<223> OTHER INFORMATION: Synthetic construct

<400> SEQUENCE: 4
atgggcagca gccatcatca tcatcatcac agcagcggcc tgtgccgcg cggcagccat    60 atgcaaaaac tactatcttt accgtccaat ctggttcagt cttttcatga actggagagg   120
gtgaatcgta ccgattggtt ttgtacttcc gacccggtag gtaagaaact tggttccggt   180
ggtggaacat cctggctgct tgaagaatgt tataatgaat attcagatgg tgctactttt   240

```
ggagagtggc ttgaaaaaga aaaaagaatt cttcttcatg cgggtgggca aagccgtcgt    300
ttacccggct atgcaccttc tggaaagatt ctcactccgg ttcctgtgtt ccggtgggag    360
agagggcaac atctgggaca aaatctgctt tctctgcaac ttcccctata tgaaaaaatc    420
atgtctttgg ctccggataa actccataca ctgattgcga gtggtgatgt ctatattcgt    480
tcggagaaac ctttgcagag tattcccgaa gcggatgtgg tttgttatgg actgtgggta    540
gatccgtctc tggctaccca tcatggcgtg tttgcttccg atcgcaaaca tcccgaacaa    600
ctcgacttta tgcttcagaa gccttcgttg gcagaattgg aatctttatc gaagacccat    660
ttgttcctga tggacatcgg tatatggctt ttgagtgacc gtgccgtaga aatcttgatg    720
aaacgttctc ataaagaaag ctctgaagaa ctaaagtatt atgatcttta ttccgatttt    780
ggattagctt tgggaactca tccccgtatt gaagacgaag aggtcaatac gctatccgtt    840
gctattctgc ctttgccggg aggagagttc tatcattacg ggaccagtaa agaactgatt    900
tcttcaactc tttccgtaca gaataaggtt tacgatcagc gtcgtatcat gcaccgtaaa    960
gtaaagccca atccggctat gtttgtccaa aatgctgtcg tgcggatacc tctttgtgcc   1020
gagaatgctg atttatggat cgagaacagt catatcggac caaagtggaa gattgcttca   1080
cgacatatta ttaccggggt tccggaaaat gactggtcat tggctgtgcc tgccggagtg   1140
tgtgtagatg tggttccgat gggtgataag ggctttgttg cccgtccata cggtctggac   1200
gatgttttca aggagatttt gagagattcc aaaacaaccc tgacgggtat tccttttggt   1260
gaatggatgt ccaaacgcgg tttgtcatat acagatttga aaggacgtac ggacgattta   1320
caggcagttt ccgtattccc tatggttaat tctgtagaag agttgggatt ggtgttgagg   1380
tggatgttgt ccgaacccga actggaggaa ggaaagaata tctggttacg ttccgaacat   1440
ttttctgcgg acgaaatttc ggcaggtgcc aatctgaagc gtttgtatgc acaacgtgaa   1500
gagttcagaa aaggaaactg gaaagcattg gccgttaatc atgaaaaaag tgtttttttat   1560 caacttgatt tggccgatgc agctgaagat tttgtacgtc ttggtttgga tatgcctgaa   1620
ttattgcctg aggatgctct gcagatgtca cgcatccata accggatgtt gcgtgcgcgt   1680 atttttgaaat tagacgggaa agattatcgt ccggaagaac aggctgcttt tgatttgctt   1740
cgtgacggct gctgacggg atcagtaat cgtaagagta ccccaaaatt ggatgtatat   1800
tccgatcaga ttgttgggg acgtagcccc gtgcgcatcg atatggcagg tggatggacc   1860
gatactcctc cttattcact ttattcggga ggaaatgtgg tgaatctagc cattgagttg   1920
aacggacaac ctcccttaca ggtctatgtg aagccgtgta aagacttcca tatcgtcctg   1980
cgttctatcg atatgggtgc tatggaaata gtatctacgt ttgatgaatt gcaagattat   2040
aagaagatcg gttcaccttt ctctattccg aaagccgctc tgtcattggc aggctttgca   2100
cctgcgtttt ctgctgtatc ttatgcttca ttagaggaac agcttaaaga tttcggtgca   2160
ggtattgaag tgactttatt ggctgctatt cctgccggtt ccggtttggg caccagttcc   2220
attctggctt ctaccgtact tggtgccatt aacgatttct gtggtttagc ctgggataaa   2280
aatgagattt gtcaacgtac tcttgttctt gaacaattgc tgactaccgg aggtggatgg   2340
caggatcagt atggaggtgt gttgcagggt gtgaagcttc ttcagaccga ggccggcttt   2400
gctcaaagtc cattggtgcg ttggctaccc gatcatttat ttacgcatcc tgaatacaaa   2460
gactgtcact tgcttttatta taccggtata actcgtacgg caaaagggat cttggcagaa   2520
atagtcagtt ccatgttcct caattcatcg ttgcatctca atttacttc ggaaatgaag   2580
```

```
gcgcatgcat tggatatgaa tgaagctata cagcgtggaa gttttgttga gtttggccgt    2640
ttggtaggaa aaacctggga acaaaacaaa gcattggata gcggaacaaa tcctccggct    2700
gtggaggcaa ttatcgatct gataaaagat tataccttgg gatataaatt gccgggagcc    2760
ggtggtggcg ggtacttata tatggtagcg aaagatccgc aagctgctgt tcgtattcgt    2820
aagatactga cagaaaacgc tccgaatccg cgggcacgtt ttgtcgaaat gacgttatct    2880
gataagggat ccaagtatc acgatcataa                                      2910

<210> SEQ ID NO 5
<211> LENGTH: 552
<212> TYPE: DNA
<213> ORGANISM: Artificial Sequence
<220> FEATURE:
<223> OTHER INFORMATION: Synthetic construct

<400> SEQUENCE: 5
atgggtttag aaaccgtacc ggcaggtaaa gcattgccag atgatattta tgttgtgatt      60
gaaattcctg ctaattcaga tccaattaaa tatgaagtgg ataagaaag tggcgcgttg     120 tttgttgacc gttttatggc gacagcgatg ttctatccag cgaactatgg ttatgtgaat     180
aacacattgt ctttagatgg tgaccccgtt gatgtattag tcccgacacc atacccatta     240
caaccgggct cagtgattcg ttgccgtcca gttggggtat taaaaatgac agatgaagct     300
ggaagtgatg cgaaagtggt ggcagtacca cacagcaaat taaccaaaga atacgatcat     360
attaaagatg tgaatgattt accggcatta ttaaaagcac aaatccaaca cttcttcgaa     420
agctacaaag cattagaagc gggtaaatgg gtgaaagtag atggttggga aggtgttgat     480
gccgcccgtc aagaaatttt agattcattt gaacgtgcaa aaaaactcga gcaccaccac     540
caccaccact ga                                                         552

<210> SEQ ID NO 6
<211> LENGTH: 29
<212> TYPE: DNA
<213> ORGANISM: Artificial Sequence
<220> FEATURE:
<223> OTHER INFORMATION: Synthetic construct

<400> SEQUENCE: 6
gatccatatg attatcgttc acctgtgcg                                        29

<210> SEQ ID NO 7
<211> LENGTH: 28
<212> TYPE: DNA
<213> ORGANISM: Artificial Sequence
<220> FEATURE:
<223> OTHER INFORMATION: Synthetic construct

<400> SEQUENCE: 7
aagggatcct tacagaacaa tccaaccc                                         28

<210> SEQ ID NO 8
<211> LENGTH: 30
<212> TYPE: DNA
<213> ORGANISM: Artificial Sequence
<220> FEATURE:
<223> OTHER INFORMATION: Synthetic construct

<400> SEQUENCE: 8
gatccatatg gtgaaagtac tgactgtatt                                       30
```

```
<210> SEQ ID NO 9
<211> LENGTH: 47
<212> TYPE: DNA
<213> ORGANISM: Artificial Sequence
<220> FEATURE:
<223> OTHER INFORMATION: Synthetic construct

<400> SEQUENCE: 9
acgcgtcgac ttagtggtgg tggtggtggt gcagaacaat ccaaccc        47

<210> SEQ ID NO 10
<211> LENGTH: 297
<212> TYPE: PRT
<213> ORGANISM: Unknown
<220> FEATURE:
<223> OTHER INFORMATION: Description of Unknown:
      FutC sequence

<400> SEQUENCE: 10
```

Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Leu Asn Thr Pro
            20                  25                  30

Val Leu Leu Asp Ile Thr Ser Phe Asp Trp Ser Asn Arg Lys Met Gln
        35                  40                  45

Leu Glu Leu Phe Pro Ile Asp Leu Pro Tyr Ala Ser Ala Lys Glu Ile
    50                  55                  60

Ala Ile Ala Lys Met Gln His Leu Pro Lys Leu Val Arg Asp Thr Leu
65                  70                  75                  80

Lys Cys Met Gly Phe Asp Arg Val Ser Gln Glu Ile Val Phe Glu Tyr
                85                  90                  95

Glu Pro Gly Ile Leu Lys Pro Ser Arg Leu Thr Tyr Phe Tyr Gly Tyr
            100                 105                 110

Phe Gln Asp Pro Arg Tyr Phe Asp Ala Ile Ser Pro Leu Ile Lys Gln
        115                 120                 125

Thr Phe Thr Leu Pro Pro Pro Glu Asn Gly Asn Asn Lys Lys Lys Glu
    130                 135                 140

Glu Glu Tyr His Arg Lys Ile Ala Leu Ile Leu Ala Ala Lys Asn Ser
145                 150                 155                 160

Val Phe Val His Val Arg Arg Gly Asp Tyr Val Gly Ile Gly Cys Gln
                165                 170                 175

Leu Gly Ile Asp Tyr Gln Lys Lys Ala Leu Glu Tyr Ile Ala Lys Arg
            180                 185                 190

Val Pro Asn Met Glu Leu Phe Val Phe Cys Glu Asp Leu Lys Phe Thr
        195                 200                 205

Gln Asn Ile Asp Leu Gly Tyr Pro Phe Met Asp Met Thr Thr Arg Asp
    210                 215                 220

Lys Glu Glu Glu Ala Tyr Trp Asp Met Leu Leu Met Gln Ser Cys Lys
225                 230                 235                 240

His Gly Ile Ile Ala Asn Ser Thr Tyr Ser Trp Ala Ala Tyr Leu
                245                 250                 255

Ile Asn Asn Pro Glu Lys Ile Ile Gly Pro Lys His Trp Leu Phe
            260                 265                 270

Gly His Glu Asn Ile Leu Cys Lys Glu Trp Val Lys Ile Glu Ser His
        275                 280                 285

Phe Glu Val Lys Ser Lys Lys Tyr Asn
    290                 295

<210> SEQ ID NO 11
<211> LENGTH: 299
<212> TYPE: PRT
<213> ORGANISM: Unknown
<220> FEATURE:
<223> OTHER INFORMATION: Description of Unknown:
      WbiQ sequence

<400> SEQUENCE: 11

Met Met Tyr Cys Cys Leu Ser Gly Gly Leu Gly Asn Gln Met Phe Gln
1               5                   10                  15

Tyr Ala Ala Ala Tyr Ile Leu Lys Gln His Phe Pro Asp Thr Ile Leu
            20                  25                  30

Val Leu Asp Asp Ser Tyr Tyr Phe Asn Gln Pro Gln Lys Asp Thr Ile
        35                  40                  45

Arg His Leu Glu Leu Asp Gln Phe Lys Ile Ile Phe Asp Arg Phe Ser
    50                  55                  60

Ser Lys Asp Glu Lys Val Lys Ile Asn Arg Leu Arg Lys His Lys Lys
65                  70                  75                  80

Ile Pro Leu Leu Asn Ser Phe Leu Gln Phe Thr Ala Ile Lys Leu Cys
                85                  90                  95

Asn Lys Tyr Ser Leu Asn Asp Ala Ser Tyr Tyr Asn Pro Glu Ser Ile
            100                 105                 110

Lys Asn Ile Asp Val Ala Cys Leu Phe Ser Phe Tyr Gln Asp Ser Lys
        115                 120                 125

Leu Leu Asn Glu His Arg Asp Leu Ile Leu Pro Leu Phe Glu Ile Arg
    130                 135                 140

Asp Asp Leu Arg Val Leu Cys His Asn Leu Gln Ile Tyr Ser Leu Ile
145                 150                 155                 160

Thr Asp Ser Lys Asn Ile Thr Ser Ile His Val Arg Arg Gly Asp Tyr
                165                 170                 175

Val Asn Asn Lys His Ala Ala Lys Phe His Gly Thr Leu Ser Met Asp
            180                 185                 190

Tyr Tyr Ile Ser Ala Met Glu Tyr Ile Glu Ser Glu Cys Gly Ser Gln
        195                 200                 205

Thr Phe Ile Ile Phe Thr Asp Val Ile Trp Ala Lys Glu Lys Phe
    210                 215                 220

Ser Lys Tyr Ser Asn Cys Leu Val Ala Asp Ala Asp Glu Asn Lys Phe
225                 230                 235                 240

Ser Val Ile Asp Met Tyr Leu Met Ser Leu Cys Asn Asn Ile Ile
                245                 250                 255

Ala Asn Ser Thr Tyr Ser Trp Trp Gly Ala Trp Leu Asn Arg Ser Glu
            260                 265                 270

Asp Lys Leu Val Ile Ala Pro Lys Gln Trp Tyr Ile Ser Gly Asn Glu
        275                 280                 285

Cys Ser Leu Lys Asn Glu Asn Trp Ile Ala Met
    290                 295

<210> SEQ ID NO 12
<211> LENGTH: 302
<212> TYPE: PRT
<213> ORGANISM: Unknown
<220> FEATURE:
<223> OTHER INFORMATION: Description of Unknown:
      WbnK sequence

<400> SEQUENCE: 12

Met Tyr Ser Cys Leu Ser Gly Gly Leu Gly Asn Gln Met Phe Gln Tyr
1               5                   10                  15

Ala Ala Ala Tyr Ile Leu Gln Arg Lys Leu Lys Gln Arg Ser Leu Val
            20                  25                  30

Leu Asp Asp Ser Tyr Phe Leu Asp Cys Ser Asn Arg Asp Thr Arg Arg
        35                  40                  45

Arg Phe Glu Leu Asn Gln Phe Asn Ile Cys Tyr Asp Arg Leu Thr Thr
50                  55                  60

Ser Lys Glu Lys Lys Glu Ile Ser Ile Ile Arg His Val Asn Arg Tyr
65                  70                  75                  80

Arg Leu Pro Leu Phe Val Thr Asn Ser Ile Phe Gly Val Leu Ile Lys
                85                  90                  95

Lys Asn Tyr Leu Pro Glu Ala Lys Phe Tyr Glu Phe Leu Asn Asn Cys
            100                 105                 110

Lys Leu Gln Val Lys Asn Gly Tyr Cys Leu Phe Ser Tyr Phe Gln Asp
        115                 120                 125

Ala Thr Leu Ile Asp Ser His Arg Asp Met Ile Leu Pro Leu Phe Gln
    130                 135                 140

Ile Asn Glu Asp Leu Leu Asn Leu Cys Asn Asp Leu His Ile Tyr Lys
145                 150                 155                 160

Lys Val Ile Cys Glu Asn Ala Asn Thr Thr Ser Leu His Ile Arg Arg
                165                 170                 175

Gly Asp Tyr Ile Thr Asn Pro His Ala Ser Lys Phe His Gly Val Leu
            180                 185                 190

Pro Met Asp Tyr Tyr Glu Lys Ala Ile Arg Tyr Ile Glu Asp Val Gln
        195                 200                 205

Gly Glu Gln Val Ile Ile Val Phe Ser Asp Asp Val Lys Trp Ala Glu
    210                 215                 220

Asn Thr Phe Ala Asn Gln Pro Asn Tyr Tyr Val Val Asn Asn Ser Glu
225                 230                 235                 240

Cys Glu Tyr Ser Ala Ile Asp Met Phe Leu Met Ser Lys Cys Lys Asn
                245                 250                 255

Asn Ile Ile Ala Asn Ser Thr Tyr Ser Trp Trp Gly Ala Trp Leu Asn
            260                 265                 270

Thr Phe Glu Asp Lys Ile Val Val Ser Pro Arg Lys Trp Phe Ala Gly
        275                 280                 285

Asn Asn Lys Ser Lys Leu Thr Met Asp Ser Trp Ile Asn Leu
    290                 295                 300

<210> SEQ ID NO 13
<211> LENGTH: 283
<212> TYPE: PRT
<213> ORGANISM: Unknown
<220> FEATURE:
<223> OTHER INFORMATION: Description of Unknown:
      WbsJ sequence

<400> SEQUENCE: 13

Met Glu Val Lys Ile Ile Gly Gly Leu Gly Asn Gln Met Phe Gln Tyr
1               5                   10                  15

Ala Thr Ala Phe Ala Ile Ala Lys Arg Thr His Gln Asn Leu Thr Val
            20                  25                  30

Asp Ile Ser Asp Ala Val Lys Tyr Lys Thr His Pro Leu Arg Leu Val
        35                  40                  45

Glu Ile Ser Cys Ser Ser Glu Phe Val Lys Lys Ala Trp Pro Phe Glu
50                  55                  60

```
Lys Tyr Leu Phe Ser Glu Lys Ile Pro His Phe Met Lys Lys Gly Met
 65                  70                  75                  80

Phe Arg Lys His Tyr Val Glu Lys Ser Leu Glu Tyr Asp Pro Asp Ile
                 85                  90                  95

Asp Thr Lys Ser Ile Asn Lys Lys Ile Val Gly Tyr Phe Gln Thr Glu
            100                 105                 110

Lys Tyr Phe Lys Glu Phe Arg His Glu Leu Ile Lys Glu Phe Gln Pro
        115                 120                 125

Lys Thr Lys Phe Asn Ser Tyr Gln Asn Glu Leu Leu Asn Leu Ile Lys
130                 135                 140

Glu Asn Asp Thr Cys Ser Leu His Ile Arg Arg Gly Asp Tyr Val Ser
145                 150                 155                 160

Ser Lys Ile Ala Asn Glu Thr His Gly Thr Cys Ser Glu Lys Tyr Phe
                165                 170                 175

Glu Arg Ala Ile Asp Tyr Ile Met Asn Lys Gly Val Ile Asn Lys Lys
            180                 185                 190

Thr Leu Ile Phe Ile Phe Ser Asp Asp Ile Lys Trp Cys Arg Glu Asn
        195                 200                 205

Ile Phe Phe Asn Asn Gln Ile Cys Phe Val Gln Gly Asp Ala Tyr His
210                 215                 220

Val Glu Leu Asp Met Leu Leu Met Ser Lys Cys Lys Asn Asn Ile Ile
225                 230                 235                 240

Ser Asn Ser Ser Phe Ser Trp Trp Ala Ala Trp Leu Asn Glu Asn Lys
                245                 250                 255

Asn Lys Thr Val Ile Ala Pro Ser Lys Trp Phe Lys Lys Asp Ile Lys
            260                 265                 270

His Asp Ile Ile Pro Glu Ser Trp Val Lys Leu
        275                 280

<210> SEQ ID NO 14
<211> LENGTH: 302
<212> TYPE: PRT
<213> ORGANISM: Unknown
<220> FEATURE:
<223> OTHER INFORMATION: Description of Unknown:
      WbwK sequence

<400> SEQUENCE: 14

Met Tyr Ser Cys Leu Ser Gly Gly Leu Gly Asn Gln Met Phe Gln Tyr
 1               5                  10                  15

Ala Ala Ala Tyr Ile Leu Gln Arg Lys Leu Lys Gln Arg Ser Leu Val
                 20                  25                  30

Leu Asp Asp Ser Tyr Phe Leu Asp Cys Ser Asn Arg Asp Thr Arg Arg
             35                  40                  45

Arg Phe Glu Leu Asn Gln Phe Asn Ile Cys Tyr Asp Arg Leu Thr Ile
         50                  55                  60

Ser Lys Glu Lys Lys Glu Ile Ser Ile Ile Arg His Val Asn Arg Tyr
 65                  70                  75                  80

Arg Leu Pro Leu Phe Val Thr Asn Ser Ile Phe Gly Val Leu Leu Lys
                 85                  90                  95

Lys Asn Tyr Leu Pro Glu Ala Lys Phe Tyr Glu Phe Leu Asn Asn Cys
            100                 105                 110

Lys Leu Gln Val Lys Asn Gly Tyr Cys Leu Phe Ser Tyr Phe Gln Asp
        115                 120                 125

Ala Thr Ile Ile Asp Ser His Arg Asp Met Ile Leu Pro Leu Phe Gln
```

```
            130                 135                 140
Ile Asn Glu Asp Leu Leu His Leu Cys Asn Asp Leu His Ile Tyr Lys
145                 150                 155                 160

Lys Val Ile Cys Glu Asn Ala Asn Thr Thr Ser Leu His Ile Arg Arg
                165                 170                 175

Gly Asp Tyr Ile Thr Asn Pro His Ala Ser Lys Phe Gly His Val Leu
                180                 185                 190

Pro Met Asp Tyr Tyr Glu Lys Ala Ile Arg Tyr Ile Glu Asp Val Gln
                195                 200                 205

Gly Glu Gln Val Ile Ile Val Phe Ser Asp Val Lys Trp Ala Glu
210                 215                 220

Asn Thr Phe Ala Asn Gln Pro Asn Tyr Tyr Val Val Asn Asn Ser Glu
225                 230                 235                 240

Cys Glu Tyr Ser Ala Ile Asp Met Phe Leu Met Ser Lys Cys Lys Asn
                245                 250                 255

Asn Ile Ile Ala Asn Ser Thr Tyr Ser Trp Trp Gly Ala Trp Leu Asn
                260                 265                 270

Thr Phe Glu Asp Lys Ile Val Val Ser Pro Arg Lys Trp Phe Ala Gly
                275                 280                 285

Asn Asn Lys Ser Lys Leu Thr Met Asp Ser Trp Ile Asn Leu
                290                 295                 300
```

<210> SEQ ID NO 15
<211> LENGTH: 297
<212> TYPE: PRT
<213> ORGANISM: Unknown
<220> FEATURE:
<223> OTHER INFORMATION: Description of Unknown:
      WbgL sequence

<400> SEQUENCE: 15

```
Met Ser Ile Ile Arg Leu Gln Gly Gly Leu Gly Asn Gln Leu Phe Gln
1               5                   10                  15

Phe Ser Phe Gly Tyr Ala Leu Ser Lys Ile Asn Gly Thr Pro Leu Tyr
                20                  25                  30

Phe Asp Ile Ser His Tyr Ala Glu Asn Asp Asp His Gly Gly Tyr Arg
                35                  40                  45

Leu Asn Asn Ile Gln Ile Pro Glu Glu Tyr Leu Gln Tyr Tyr Thr Pro
50                  55                  60

Lys Ile Asn Asn Ile Tyr Lys Leu Leu Val Arg Gly Ser Arg Leu Tyr
65                  70                  75                  80

Pro Asp Ile Phe Leu Phe Leu Gly Phe Cys Asn Glu Phe His Ala Tyr
                85                  90                  95

Gly Tyr Asp Phe Glu Tyr Ile Ala Gln Lys Trp Lys Ser Lys Lys Tyr
                100                 105                 110

Ile Gly Tyr Trp Gln Ser Glu His Phe Phe His Lys His Ile Ile Asp
                115                 120                 125

Leu Lys Glu Phe Phe Ile Pro Lys Asn Val Ser Glu Gln Ala Asn Leu
130                 135                 140

Leu Ala Ala Lys Ile Ile Glu Ser Gln Ser Ser Leu Ser Ile His Ile
145                 150                 155                 160

Arg Arg Gly Asp Tyr Ile Lys Asn Lys Thr Ala Thr Ile Thr His Gly
                165                 170                 175

Val Cys Ser Leu Glu Tyr Tyr Lys Lys Ala Leu Asn Lys Ile Arg Asp
                180                 185                 190
```

```
Leu Ala Met Ile Arg Asp Val Phe Ile Phe Ser Asp Ile Phe Trp
            195                 200                 205

Cys Lys Glu Asn Ile Glu Thr Leu Leu Ser Lys Lys Tyr Asn Ile Tyr
    210                 215                 220

Tyr Ser Glu Asp Leu Ser Gln Glu Glu Asp Leu Trp Leu Met Ser Leu
225                 230                 235                 240

Ala Asn His His Ile Ile Ala Asn Ser Ser Phe Ser Trp Trp Gly Ala
                245                 250                 255

Tyr Leu Gly Ser Ser Ala Ser Gln Ile Val Ile Tyr Pro Thr Pro Trp
            260                 265                 270

Tyr Asp Ile Thr Pro Lys Asn Thr Tyr Ile Pro Ile Val Asn His Trp
            275                 280                 285

Ile Asn Val Asp Lys His Ser Ser Cys
    290                 295

<210> SEQ ID NO 16
<211> LENGTH: 11
<212> TYPE: PRT
<213> ORGANISM: Thermosynechococcus elongatus

<400> SEQUENCE: 16

Gly Gly Leu Gly Asn Gln Met Phe Gln Tyr Ala
1               5                   10

<210> SEQ ID NO 17
<211> LENGTH: 9
<212> TYPE: PRT
<213> ORGANISM: Thermosynechococcus elongatus

<400> SEQUENCE: 17

Ser Leu His Ile Arg Arg Gly Asp Tyr
1               5

<210> SEQ ID NO 18
<211> LENGTH: 8
<212> TYPE: PRT
<213> ORGANISM: Thermosynechococcus elongatus

<400> SEQUENCE: 18

Val Phe Ser Asp Asp Pro Gln Trp
1               5

<210> SEQ ID NO 19
<211> LENGTH: 40
<212> TYPE: PRT
<213> ORGANISM: Thermosynechococcus elongatus

<400> SEQUENCE: 19

Asp Met Gln Leu Met Ser Ala Cys Arg His His Ile Ile Ala Asn Ser
1               5                   10                  15

Thr Phe Ser Trp Trp Gly Ala Trp Leu Asn Pro Arg Pro Asp Lys Val
            20                  25                  30

Val Ile Ala Pro Arg His Trp Phe
        35                  40
```

REACTION MIXTURE FOR SYNTHESIS OF ALPHA1-2-FUCOSIDES

CROSS-REFERENCES TO RELATED APPLICATIONS

This application is a US National Phase Application Under 371 of PCT/US2016/067601 filed Dec. 19, 2016, which claims priority to U.S. Provisional Application No. 62/269,574, filed Dec. 18, 2015, each of which is incorporated in its entirety herein for all purposes.

REFERENCE TO BIOLOGICAL SEQUENCE DISCLOSURE

The instant application contains a Sequence Listing which has been submitted in .txt format via EFS-Web in accordance with 37 C.F.R. §§ 1.821- to 1.825, and is hereby incorporated by reference in its entirety for all purposes. The Sequence Listing written in txt. format is named 076916_1092311_215510US_SequenceListing.TXT, was created on Aug. 11, 2021 and is 35,212 bytes in size.

STATEMENT AS TO RIGHTS TO INVENTIONS MADE UNDER FEDERALLY SPONSORED RESEARCH AND DEVELOPMENT

This invention was made with government support under Grant No. HD065122, awarded by the National Institutes of Health. The government has certain rights in the invention.

BACKGROUND OF THE INVENTION

L-Fucose is commonly found as a component of glycans in glycoconjugates on mammalian cell surface where they play important functions.[1] Among fucose-containing mammalian glycoconjugates in which fucose can be α1-2/3/4/6-linked to galactose (Gal), N-acetylglucosamine (GlcNAc), glucose (Glc), or α-linked to the serine or threonine residues in proteins,[2] α1-2-linked fucose is a major structural component of all human histo-blood group ABH antigens and some Lewis antigens such as Lewis b and Lewis y.[1] α1-2-Linked fucosides are also abundant in human milk oligosaccharides (HMOS) where they have been found to have prebiotic, antiadhesive antimicrobial, and immunomodulating activities which contribute significantly to the benefits of breast feeding.[3] For example, *Campylobacter jejuni* (*C. jejuni*), one of the most common causes of diarrhea worldwide and the primary cause of ascending motor neuron paralysis,[4] binds α 1-2-fucosylated blood group H antigens. The fucosides in HMOS can inhibit *C. jejuni* binding to host cells thereby blocking the infection process.[4-5]

In humans, FUT1[6] is an α1-2-fucosyltransferase (h2FT) responsible for synthesizing the Fucα1-2GalβOR linkage in ABH antigens presented in glycoproteins and glycolipids on red blood cell surface. FUT2,[7] also known as the Secretor (Se) transferase, is another h2FT that is responsible for the synthesis of α1-2-fucose-containing glycan structures in body fluids. The lack of FUT2 determines the non-secretor status and the consequent lacking of α1-2-linked fucose in body fluids such as the absence of Fucα1-2Gal-containing structures including 2'-fucosyllactose (2'FL),[8] lactodifucotetraose (LDFT), lacto-N-fucopentaose I (LNFP I), and lacto-N-difuco-hexaose I (LNDFH I) in the milk of Le$^{a+b-}$ non-secretors.[9]

Some bacteria which are often commensals or pathogens of human and animals also have fucosyltransferases that are involved in the synthesis of α1-2-linked fucose-containing lipopolysaccharides (LPSs). Several bacterial α1-2-fucosyltransferases (2FTs) have been cloned, characterized, and used for small-scale synthesis of α1-2-fucosides. These include *Helicobacter pylori* (*H. pylori*) FutC (or Hp2FT),[10] *Escherichia coli* (*E. coli*) O86:B7 WbwK,[11] *E. coli* O86:K62:H2 WbnK,[12] *E. coli* O128 WbsJ,[13] and *E. coli* O127:K63(B8) WbiQ.[14] However, their expression levels are usually low which limits their application in synthesis. A more recently characterized *E. coli* O126 WbgL[15] has a reasonable expression level but has a preference towards β1-4-linked galactosides as acceptor substrates. The access to α1-2-fucosylated α1-3-linked galactosides in large scales has been greatly hampered by the lack of an α2FT that can be obtained in large amounts.

BRIEF SUMMARY OF THE INVENTION

In a first aspect, the invention provides a reaction mixture containing an α1-2-fucosyltransferase enzyme having a sequence identity of at least about 62% to the α1-2-fucosyltransferase of SEQ ID NO:1 (Te2FT) and a bifunctional L-fucokinase/GDP-fucose pyrophosphorylase enzyme, or an inorganic pyrophosphatase enzyme, or the combination thereof. In some embodiments, the α1-2-fucosyltransferase enzyme has a sequence identity of at least about 90%, 91%, 92%, 93%, 94%, 95%, 96%, 97%, 98%, or 99%, or is identical to SEQ ID NO:1. In some embodiments, the bifunctional L-fucokinase/GDP-fucose pyrophosphorylase enzyme is BfFKP from *Bacteroides fragilis* strain NCTC9343. In some embodiments, the inorganic pyrophosphatase enzyme is PmPpA from *Pasteurella multocida*. In certain embodiments, the reaction mixture further comprises guanidine 5'-diphosphate-fucose (GDP-Fucose).

In a second aspect, the invention provides an expression cassette comprising a heterologous promoter operably linked to a nucleic acid encoding an α1-2-fucosyltransferase. In some embodiments, the α1-2-fucosyltransferase has a sequence identity of at least about 62% to SEQ ID NO:1. In some embodiments, the α1-2-fucosyltransferase comprises high α1-2-fucosyltransferase activity and low donor hydrolysis activity. In certain embodiments, the α1-2-fucosyltransferase includes an enzyme having an α1-2-fucosyltransferase activity that is at least 2-fold, 3-fold, 4-fold, or 5-fold more than the α1-2-fucosyltransferase activity of GST-WbsJ, His$_6$Prop-WgbL, and Hp2FT, and wherein the α1-2-fucosyltransferase activity is measured as the k$_{cat}$ value for GDP-fucose.

In a third aspect, the invention provides a method of making an α1-2-fucosyltransferase. In some embodiments, the method includes incubating a host cell comprising an expression cassette comprising a heterologous promoter operably linked to a nucleic acid encoding an α1-2-fucosyltransferase having a sequence identity of at least about 62% to SEQ ID NO:1, in culture media under conditions suitable for producing the α1-2-fucosyltransferase and isolating the α1-2-fucosyltransferase from the host cell or spent media.

BRIEF DESCRIPTION OF THE DRAWINGS

FIG. 1 shows the amino acid sequence alignment of Te2FT (UniProtKB:Q8DK72, GenBank: BAC08546.1, SEQ ID NO:1), *H. pylori* FutC (UniProtKB:A4L7J1, SEQ ID NO:10), *E. coli* O127:K63 WbiQ (UniProtKB:Q5J7C6, SEQ ID NO:11), *E. coli* O86:K62:H2 WbnK (UniProtKB: Q58YV9, SEQ ID NO:12), *E. coli* O128:B12 WbsJ (UniProtKB:Q6XQ53, SEQ ID NO:13), *E. coli* O86:B7 WbwK (GenBank:AAO37719.1, SEQ ID NO:14), and *E. coli* O126 WbgL (UniProtKB: A6M9C2, SEQ ID NO:15).

DETAILED DESCRIPTION OF THE INVENTION

I. General

Figure 2:
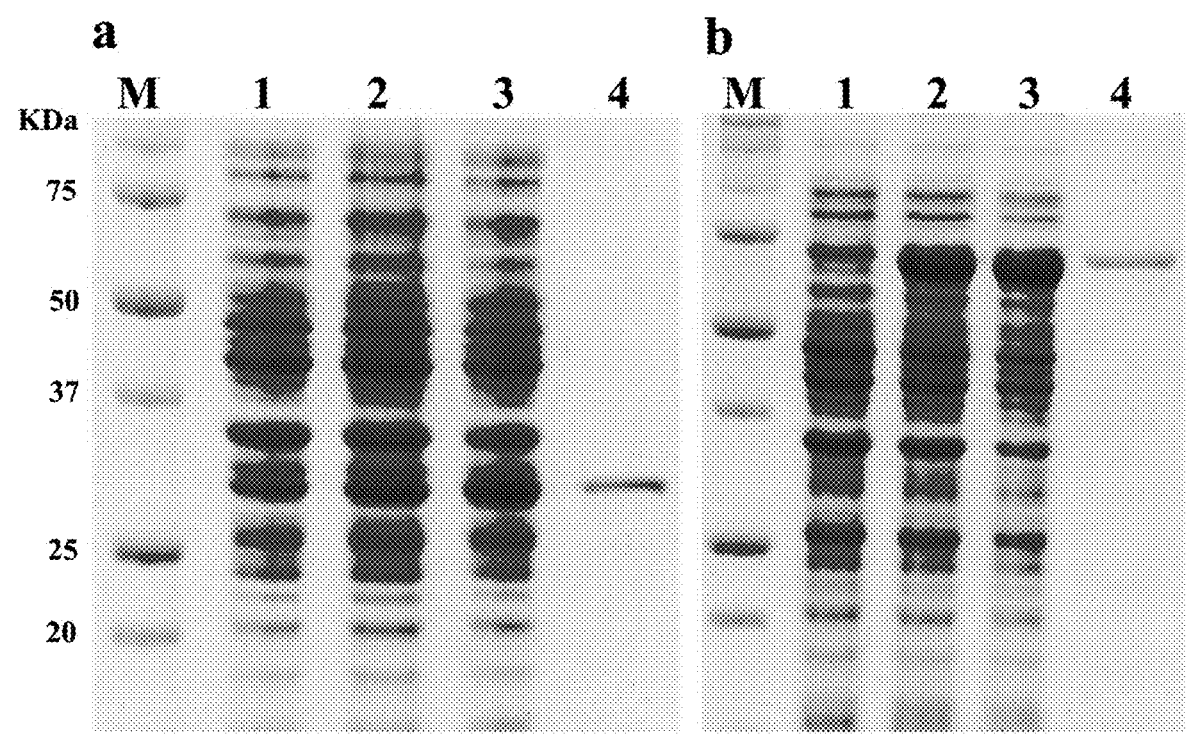
FIG. 2 shows the SDS-PA(3E (12% Tris-Glycine gel) analysis of His$_6$-Te2FT (a) and MBP-Te2FT-His$_6$ (b) expression and purification. Lanes: M, protein standards; 1, whole cell extraction before induction; 2, whole cell extraction after induction; 3, cell lysate after induction; 4, Ni$^{2+}$-column purified protein.
Figure 3:
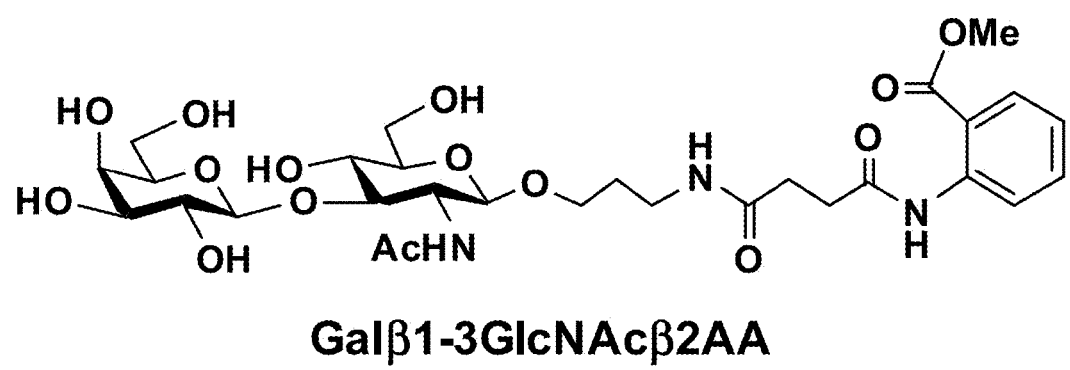
FIG. 3 shows the structure of Galβ1-3GlcNAcβ2AA used as an acceptor substrate for Te2FT.

The present invention provides a fucosyltransferase useful for the preparation of fucosylated molecules. In particular, a α1-2-fucosyltransferase from a thermophilic cyanobacterium, *Thermosynechococcus elongatus* BP-1 (Te2FT; GenBank Accession No: NP_681784.1 GI: 22298537 encoded by gene tll0994) was demonstrated to possess high fucosyltransferase activity and low donor hydrolysis activity. Te2FT was obtained in high yield, making this enzyme highly desirable for large-scale synthesis of α1-2-fucosylated products. Te2FT was expressed and utilized in a one pot multienzyme (OPME) fucosylation system for high-yield synthesis of human blood group H antigens and a human milk oligosaccharide, lacto-N-fucopentaose I (LNFP I). The surprising superior characteristics of Te2FT as compared to other α1-2-fucosyltransferases is particularly advantageous, allowing for the preparation of a variety of fucose-containing glycoconjugates.

II. Definitions

Figure 1:
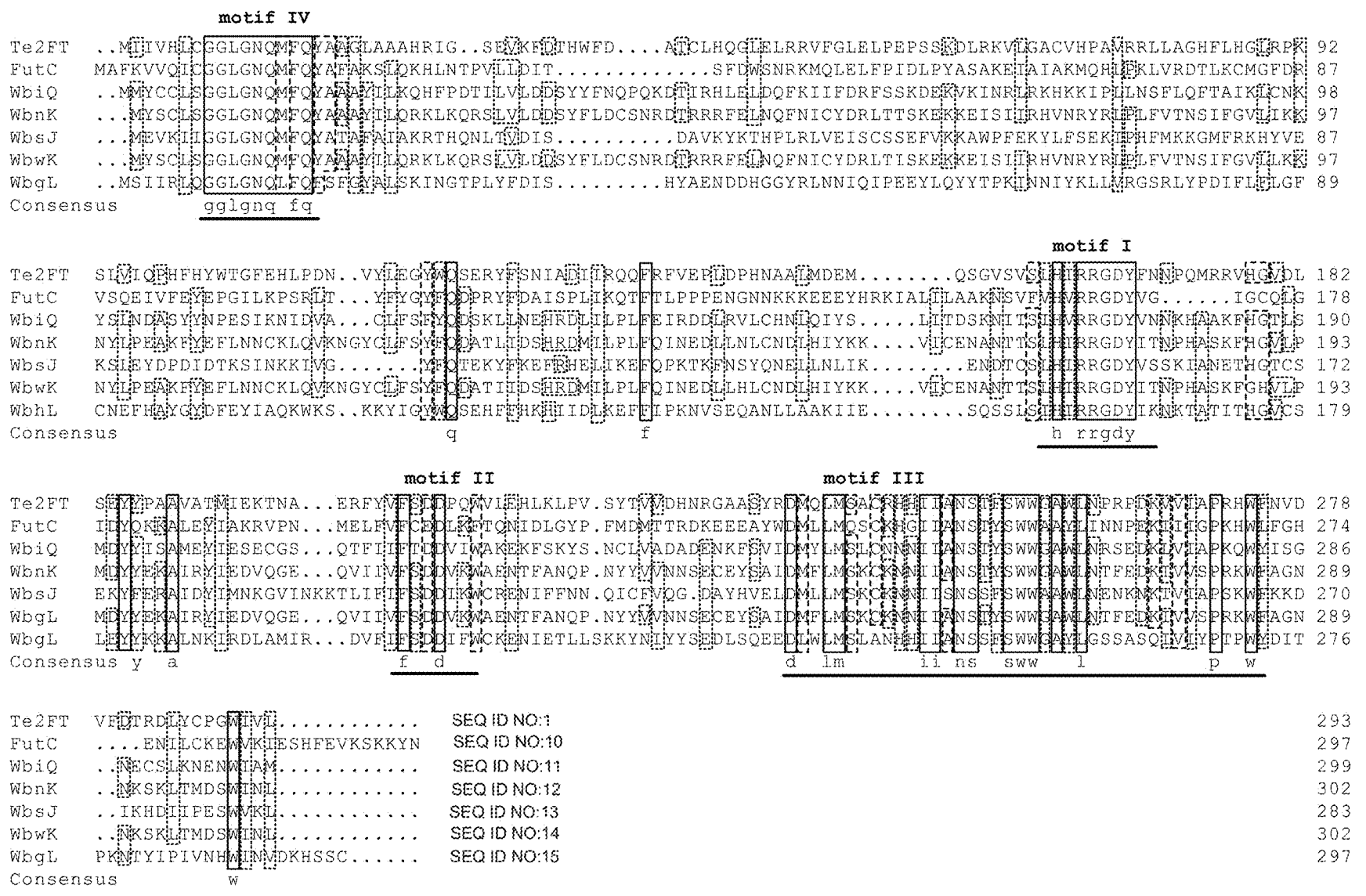

As used herein, the term "Fucosyltransferase", refers to a polypeptide that catalyzes the transfer of a fucosyl moiety from a donor substrate to an acceptor or acceptor sugar. The covalent linkage between the fucosyl moiety and the acceptor sugar can be a 1-4 linkage, a 1-3 linkage, a 1-6-linkage, or a 1-2 linkage. The linkage may be in the α- or β-configuration with respect to the anomeric carbon of the monosaccharide. In certain embodiments, the fucosyltransferases useful in the present invention include α1-2-fucosyltransferases (2FTs). In some embodiments, the fucosyltransferases useful in the present invention include those in glycosyltransferase family 11 (GT11) using Carbohydrate-Active enZYme database (CAZy) nomenclature) (see FIG. 1), and in particular *Helicobacter pylori* (*H. pylori*) FutC (or Hp2FT), *Escherichia coli* (*E. coli*) O86:B7 WbwK, *E. coli* O86:K62:H2 WbnK, *E. coli* O128 WbsJ, *E. coli* O127:K63 (B8) WbiQ, and *E. coli* O126 WbgL. In some embodiments, fucosyltransferases include, but are not limited to, galactoside 2-alpha-L-fucosyltransferases in family EC 2.4.1.69. In certain embodiments, fucosyltransferases useful in the present invention include FUT1 and FUT2. In one embodiment, the fucosyltransferases useful in the present invention include *Dictyostelium discoideum* α1-2FT. In some embodiments, a fucosyltransferase useful in the present invention includes Te2FT.

As used herein, the term "donor," in the context of a fucosyltransferase reaction refers to a compound having a nucleotide and the fucosyl sugar moiety that is added to the acceptor, where the sugar and nucleotide are covalently bound together. The sugar can be fucose or analogs thereof. The nucleotide can be any suitable nucleotide such as guanidine 5'-diphosphate-fucose (GDP)-fucose.

As used herein, the term "donor substrate", refers to a compound having a nucleotide and a sugar moiety that is added to an acceptor, where the sugar moiety and nucleotide are covalently bound together. In general, the sugar moiety is characterized by monosaccharide core having a linear formula of H(CHOH)$_n$(CO)(CHOH)$_m$H, wherein the sum of n and m is at least 2. In certain embodiments, the sum of n and m is 5. In certain embodiments, n is 5 and m is 0. Any H or OH group in the monosaccharide core can be replaced by an amine group NHR', wherein R' is selected from H, alkyl, and acyl. One of skill in the art will appreciate that the monosaccharide core can be in the linear form or in the cyclic, hemiacetal form. The hemiacetal can be a pyranose (i.e., a six-membered ring) or a furanose (i.e., a five-membered ring). In general, the hydroxyl group at the anomeric carbon of the hemiacetal is the point of connection between the sugar moiety and the nucleotide in the donor substrate. The monosaccharide core of the sugar moiety can be substituted with various functional groups as described herein. In certain embodiments, the sugar moiety is fucose or an analog thereof. The nucleotide in the donor substrate can be any suitable nucleotide, such as guanidine-5'-diphosphate (GDP).

As used herein, the term "donor substrate hydrolysis", refers to hydrolysis of an O-glycosidic bond of the sugar and the phosphate in the nucleotide-sugar donor substrate.

As used herein, the term "acceptor," in the context of a fucosyltransferase reaction refers to a substance (e.g., a glycosylated amino acid, a glycosylated protein, an oligosaccharide, or a polysaccharide) containing a sugar that accepts a fucosyl moiety from guanidine-5'-diphosphate-fucose (GDP-fucose), or a derivative thereof, during a fucosyltransferase reaction. The sugar of the acceptor glycoside can be a monosaccharide or an oligosaccharide as defined herein. In certain embodiments, the acceptor contains a glucosamine moiety, wherein the hydroxyl group at the anomeric carbon of the glucopyranose ring is the point of connection to the remainder of the glycoside. In some embodiments, the glucosamine moiety is an α-linked N-acetylglucosamine moiety. In certain embodiments, the acceptor contains a β1-3-linked glycoside, such as a β1-3-linked galactoside. In some embodiments, suitable acceptor substrates include, but are not limited to, Galβ1-3GlcNAcβ2AA, Galβ1-4GlcNAcβ2AA, and Galβ1-4Glcβ2AA. In certain embodiments, suitable acceptor substrates include, but are not limited to, Galβ1-3GlcNAcβOR, Galβ1-3GlcNAcαOR, Galβ1-3GalNAcαOR, and Galβ1-3GalNAcβOR. In some embodiments, suitable acceptors of the invention include but are not limited to, Galβ1-3GalNAcαProN$_3$, Galβ1-3GalNAcβProN$_3$, Galβ1-3GlcNAcαProN$_3$, Galβ1-3GlcNAcβProN$_3$ and lacto-N-tetraose.

As used herein, the term "pyrophosphatase", (abbreviated as PpA) refers to a polypeptide that catalyzes the conversion of pyrophosphate (i.e., $P_2O_7^{4-}$, $HP_2O_7^{3-}$, $H_2P_2O_7^{2-}$, $H_3P_2O_7$) to two molar equivalents of inorganic phosphate (i.e., $PO_4^{3-}$, $HPO_4^{2-}$, $H_2PO_4$).

As used herein, the term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

As used herein, the term "amino acid", refers to any monomeric unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (H is or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002), which is incorporated by reference. Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466, which are both incorporated by reference). The term "amino acid" also includes unnatural amino acids, modified amino acids (e.g., having modified side chains and/or backbones), and amino acid analogs.

As used herein, the term "polypeptide," "peptide," and "protein", are used interchangeably herein to refer to a polymer of amino acid residues. All three teams apply to amino acid polymers in which one or more amino acid residue is an artificial chemical mimetic of a corresponding naturally occurring amino acid, as well as to naturally occurring amino acid polymers and non-natural amino acid polymers. As used herein, the terms encompass amino acid chains of any length, including full-length proteins, wherein the amino acid residues are linked by covalent peptide bonds.

As used herein, the term "nucleic acid" or "polynucleotide", refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

As used herein, the term "mutant," in the context of fucosyltransferases of the present invention, means a polypeptide, typically recombinant, that comprises one or more amino acid substitutions relative to a corresponding, naturally-occurring or unmodified fucosyltransferase, such as an α1-2 fucosyltransferase.

As used herein, a nucleic acid is "operably linked", when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

As used herein, the terms "identical" or percent "identity," in the context of describing two or more polynucleotide or amino acid sequences, refer to two or more sequences or subsequences that are the same or have a specified percentage of amino acid residues or nucleotides that are the same. For example, a sequence can have at least 80% identity, preferably 85%, 90%, 91%, 92%, 93%, 94%, 95%, 96%, 97%, 98%, 99%, or 100% identity, to a reference sequence when compared and aligned for maximum correspondence over a comparison window, or designated region as measured using a sequence comparison algorithm or by manual alignment and visual inspection. Such sequences are then said to be "substantially identical." With regard to polynucleotide sequences, this definition also refers to the complement of a test sequence. With regard to amino acid sequences, preferably, the identity exists over a region that is at least about 50 amino acids or nucleotides in length, or more preferably over a region that is 75-100 amino acids or nucleotides in length, or most preferably over the entirety of the query molecule, e.g., all 293 amino acids of SEQ ID NO:1.

As used herein, the term "percent sequence identity", is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "similarity", or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more preferably over a region that is 75-100 amino acids in length, or most preferably over the entirety of the query molecule, e.g., all 293 amino acids of SEQ ID NO:1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

As used herein, a "comparison window", includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Algorithms suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

As used herein, the term "recombinant," refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant fucosyltransferase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

As used herein, "heterologous", refers to two or more compositions (e.g., polynucleotides, proteins, cells, etc.) that are not found together in nature. In the context of promoters operably linked to a polynucleotide, a "heterologous promoter" refers to a promoter that would not be so operably linked to the same polynucleotide as found in a product of nature (i.e., in a wild-type organism). In the context of two or more proteins, a "heterologous protein" or enzyme refers to a protein or enzyme that does not naturally exist in, or is not naturally produced by, the same organism.

As used herein, the term "vector", refers to a piece of DNA, typically double-stranded, which may have inserted into it a piece of foreign DNA. The vector may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors (i.e., expression cassettes) additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

As used herein, the term "forming a reaction mixture", or "reaction mixture", refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "oligosaccharide", refers to a compound containing at least two sugars covalently linked together. Oligosaccharides include disaccharides, trisaccharides, tetrasachharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, and 6-carbons.

As used herein, the term "BfFKP", or "bifunctional L-fucokinase GDP-fucose pyrophosphorylase", refers to a polypeptide having both L-fucokinase and GDP-L-Fuc pyrophosphorylase activity. Fucosyltransferases catalyze the transfer of fucose, or analogs thereof, from a fucose-donor substrate to the terminal sugar of an acceptor substrate. Representative fucosyltransferases include, but are not limited to, galactoside 2-alpha-L-fucosyltransferases in family EC 2.4.1.69. In certain embodiments, BfFKP's can generate GDP-L-Fuc from L-Fuc, ATP, and GTP as the starting substrates. Recombinant forms of BfFKP are well known in the art, such as the recombinant form identified in *Arabidposis*, designated AtFKGP (see, Kotake et al., JBC, 2008, 8125-8135).

As used herein, the term "glycoconjugate", refers to a carbohydrate covalently linked with other chemical species such as proteins, lipids, saccharides. Examples of glycoconjugates include, but are not limited to, glycoproteins, glycopeptides, peptidoglycans, glycolipids, glycosides and lipopolysaccharides. A glycoconjugate is formed by an enzymatic reaction, termed glycosylation. A glycoside refers to a sugar molecule, such as fucose, bound through its anomeric carbon to another group via a glycosidic bond. An example of a glycoside is one formed by an Te2FT-catalyzed reaction. In certain embodiments, a glycoconjugate of the instant invention includes, but is not limited to, α1-2fucosides. In some embodiments, a glycoconjugate of the instant invention includes, but is not limited to, Fucα1-2Galβ1-3GcNAcβProN$_3$, Fucα1-2Galβ1-3GlcNAcαProN$_3$, Fucα1-2Galβ1-3GalNAcβProN$_3$, and Fucα1-2Galβ1-3GalNAcαProN$_3$. In one embodiment, a glycoconjugate of the instant invention includes, but is not limited to, lacto-N-fucopentaose I.

As used herein, "acceptor glycoconjugate", refers to a carbohydrate that accepts a sugar moiety from a donor substrate. In certain embodiments, the acceptor glycoconjugate contains a galactoside moiety, wherein the hydroxyl group at the anomeric carbon of the galactopyranose ring is the point of connection to the remainder of the glycoconjugate. In some embodiments, the galactoside moiety is a β1-4-linked galactoside moiety or a β1-3-linked galactoside moiety. In some embodiments, the acceptor glycoconjugate comprises a Galβ1-3GlcNAc moiety, or a Galβ1-3GalNAc moiety. In one embodiment, an acceptor glycoconjugate of the instant invention includes, but is not limited to, Galβ1-3GlcNAcβ2AA, Galβ1-4GlcNAcβ2AA, and Galβ1-4Glcβ2AA. In some embodiments, an acceptor glycoconjugate of the instant invention includes, but is not limited to, Galβ1-3GlcNAcβOR, Galβ1-3GlcNAcαOR, Galβ1-3GalNAcαOR, and Galβ1-3GalNAcβOR. In one embodiment, an acceptor glycoconjugate of the instant invention includes, but is not limited to, Galβ1-3GalNAcαProN$_3$, Galβ1-3GalNAcβProN$_3$, Galβ1-3GlcNAcαProN$_3$, Galβ1-3GlcNAcβProN$_3$ or lacto-N-tetraose.

III. Fucosyltransferases

Fucosyltransferases are one class of glycosyltransferases, enzymes that catalyze the transfer of a sugar from a nucleotide-sugar (donor substrate) to an acceptor (e.g., a natural product, a monosaccharide, an oligosaccharide, a glycolipid, a glycoprotein, or a hydroxyl-containing compounds). Specifically, fucosyltransferases catalyze the transfer of fucose, or analogs thereof, from a fucose-donor substrate to the terminal sugar of an acceptor substrate. Representative fucosyltransferases include, but are not limited to, galactoside 2-alpha-L-fucosyltransferases in family EC 2.4.1.69. The fucosyltransferases of the present invention also include those of the CAZy GT11 family, or EC 2.4.1.69 made up of α1-2 fucosyltransferases. Representative GT11 fucosyltransferases include, but are not limited to, Te2FT, *Helicobacter pylori* (*H. pylori*) FutC (or Hp2FT), *Escherichia coli* (*E. coli*) O86:B7 WbwK, *E. coli* O86:K62:H2 WbnK, *E. coli* O128 WbsJ, *E. coli* O127:K63(B8) WbiQ, and *E. coli* O126 WbgL. The fucosyltransferases of the present invention also include FUT1, FUT2, FUT4, FUT6 and *Dictyostelium discoideum* α1-2FT (See Vries et al., Glycobiology, 2001, 11, 119R-128R for a review of fucosyltransferases). Te2FT is a preferred fucosyltransferase in some embodiments of the invention.

In general, the fucosyltransferases of the present invention are α1-2-fucosyltransferases. The α1-2-fucosyltransferases of the present invention can include fucosyltransferases of *Thermosynechococcus elongatus*. The fucosyltransferases include those having increased α1-2 fucosylase activity compared to a control α1-2-fucosyltransferase (e.g., *E. coli* O86:K62:H2 Wbnk, *E. coli* Wbsj or *E. coli* O127:K63(B8) WbiQ). The fucosyltransferases include those having decreased hydrolytic activity on donor substrates compared to the hydrolytic activity observed with other α1-2-fucosyltransferases on donor substrates (e.g., GDP-fucose). α1-2-fucosyltransferase activity, in particular, refers to the cleavage of the glycosidic bond between the fucose moiety from the donor substrate and the sugar of the acceptor molecule. For certain fucosyltransferases, this activity is low enough that it limits their application in large-scale synthesis.

The fucosyltransferases of the present invention can include a polypeptide having any suitable percent identity to a reference sequence (e.g., SEQ ID NO:1). For example, the fucosyltransferases of the present invention can include a polypeptide having a percent sequence identity to SEQ ID NO:1 of at least 20, 30, 40, 50, 55, 60, 65, 70, 75, 80, 85, 90, 91, 92, 93, 94, 95, 96, 97, 98 or at least 99%. In some embodiments, percent sequence identity can be at least 80%. In some embodiments, percent sequence identity can be at least 90%. In some embodiments, percent sequence identity can be at least 95%. In some embodiments, the fucosyltransferase has a sequence identity of at least about 90%, 91%, 92%, 93%, 94%, 95%, 96%, 97%, 98% or 99%, or is identical to SEQ ID NO: 1. In some embodiments, the invention provides an isolated or purified polypeptide including an amino acid sequence selected from SEQ ID NO:1 (Te2FT), $His_6$-Te2FT, and MBP-Te2FT-$His_6$.

The precise length of the fucosyltransferases can vary, and certain variants can be advantageous for expression and purification of the enzymes with high yields. For example, removal of certain peptide subunits from the overall polypeptide sequence of a fucosyltransferase can improve solubility of the enzyme and increase expression levels. Alternatively, addition of certain peptide or protein subunits to a fucosyltransferase polypeptide sequence can modulate expression, solubility, activity, or other properties. The fucosyltransferases of the present invention can include point mutations at any position of the Te2FT sequence (i.e., SEQ ID NO:1) or a Te2FT variant (e.g., a fusion protein or a truncated form). The mutants can include any suitable amino acid other than the native amino acid. For example, the amino acid can be V, I, L, M, F, W, P, S, T, A, G, C, Y, N, Q, D, E, K, R, or H. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention.

The fucosyltransferases of the present invention can be constructed by mutating the DNA sequences that encode the corresponding unmodified fucosyltransferase (e.g., a wild-type fucosyltransferase such as SEQ ID NO:1 or a corresponding variant), such as by using techniques commonly referred to as site-directed mutagenesis. Nucleic acid molecules encoding the unmodified form of the fucosyltransferase can be mutated by a variety of techniques well-known to one of ordinary skill in the art. (See, e.g., PCR Strategies (M. A. Innis, D. H. Gelfand, and J. J. Sninsky eds., 1995, Academic Press, San Diego, Calif.) at Chapter 14; PCR Protocols: A Guide to Methods and Applications (M. A. Innis, D. H. Gelfand, J. J. Sninsky, and T. J. White eds., Academic Press, N Y, 1990).

By way of non-limiting example, the two primer system, utilized in the Transformer Site-Directed Mutagenesis kit from Clontech, may be employed for introducing site-directed mutants into a polynucleotide encoding an unmodified form of the fucosyltransferase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Mutagenesis can also be conducted using a QuikChange multisite-directed mutagenesis kit (Stratagene) and the like. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) or strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutated protein). The set of cleavage fragments is fractionated by, for example, HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

IV. Bifunctional L-Fucokinase/GDP-Fucose Pyrophosphorylases

Bifunctional L-fucokinase/GDP-fucose pyrophosphorylases (BfFKP) are a class of enzymes that catalyze two steps of the L-fucose salvage pathway for the generation of activated GDP-L-fucose, L-fucokinase (EC 2.7.1.52 fucokinase) catalyzes the phosphorylation of L-fucose to form L-fucose 1-phosphate (Ishihara et al., J. Biol. Chem., 1968, 243, 1103-1109). This enzyme is the first enzyme in the utilization of free L-fucose in glycoconjugate synthesis. L-fucokinase has substrate specificity for L-fucose and ATP. GDP-fucose pyrophosphorylase (EC 2.7.7.30 fucose-1-phosphate guanylyltransferase) catalyzes the condensation of guanosine triphosphate and L-fucose 1-phosphate to form GDP-L-fucose (Ishihara and Heath, J. Biol. Chem., 1968, 243, 1110-1115). GDP-fucose pyrophosphorylase has substrate specificity for L-fucose 1-phosphate and GTP. BfFKP mutants have been observed to have about forty times more L-fucose than wild-type *Arabidopsis* plants, but the levels of other monosaccharides do not appear to differ significantly (see Kotake et al, supra). Accordingly, representative BfFKP's of the instant invention include, but are not limited to, fucokinases in family EC 2.7.1.52 and fucose-1-phosphate guanylyltransferases in family EC 2.7.7.30. BfFKPs of the present invention also include, but are not limited to, AtFKGP (*Arabidopsis thaliana*). In one embodiment, BfFKP from *Bacteroides fragilis* strain NCTC 9343 is a preferred BfFKP of the invention.

The BfFKPs of the present invention can include a polypeptide having any suitable percent identity to a reference sequence (e.g., SEQ ID NO:2). For example, the BfFKP of the present invention can include a polypeptide having a percent sequence identity to SEQ ID NO:2 of at least 20, 30, 40, 50, 55, 60, 65, 70, 75, 80, 85, 90, 91, 92, 93, 94, 95, 96, 97, 98 or at least 99% as long as the polypeptide retains the ability to catalyze the phosphorylation of L-fucose and condensation thereof, with GTP to form GDP-L-fucose. In some embodiments, percent sequence identity can be at least 80%. In some embodiments, percent sequence identity can be at least 90%. In some embodiments, percent sequence identity can be at least 95%. In some embodiments, the BfFKP has a sequence identity of at least about 90%, 91%, 92%, 93%, 94%, 95%, 96%, 97%, 98% or 99%, or is identical to SEQ ID NO: 2. In some embodiments, the invention provides an isolated or purified polypeptide including an amino acid sequence such as SEQ ID NO:2 ($His_6$-BfFKP, where the His tag is underlined).

The precise length of the BfFKP can vary, and certain variants can be advantageous for expression and purification of the enzymes with high yields. For example, removal of certain peptide subunits from the overall polypeptide sequence of a BfFKP can improve solubility of the enzyme and increase expression levels. Alternatively, addition of certain peptide or protein subunits to a BfFKP polypeptide sequence can modulate expression, solubility, activity, or other properties (see Kotake et al., supra). The BfFKP of the present invention can include point mutations at any position of the BfFKP sequence (i.e., SEQ ID NO:2) or a BfFKP variant (e.g., a fusion protein or a truncated form). The mutants can include any suitable amino acid other than the native amino acid. For example, the amino acid can be V, I, L, M, F, W, P, S, T, A, G, C, Y, N, Q, D, E, K, R, or H. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention.

The BfFKP's of the present invention can be constructed by mutating the DNA sequences that encode the corresponding unmodified BfFKP (e.g., a BfFKP such as SEQ ID NO:4 or a corresponding variant; SEQ ID NO: 4 contains a His tag, which is underlined), such as by using techniques commonly referred to as site-directed mutagenesis. Nucleic acid molecules encoding the unmodified form of the BfFKP can be mutated by a variety of techniques well-known to one of ordinary skill in the art. (See, e.g., PCR Strategies (M. A. Innis, D. H. Gelfand, and J. J. Sninsky eds., 1995, Academic Press, San Diego, Calif.) at Chapter 14; PCR Protocols: A Guide to Methods and Applications (M. A. Innis, D. H. Gelfand, J. J. Sninsky, and T. J. White eds., Academic Press, N Y, 1990).

By way of non-limiting example, the two primer system, utilized in the Transformer Site-Directed Mutagenesis kit from Clontech, may be employed for introducing site-directed mutants into a polynucleotide encoding an unmodified form of the BfFKP. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of E. coli. Plasmid DNA is isolated from the transformed bacteria, restricted with the relevant restriction enzyme (thereby linearizing the unmutated plasmids), and then retransformed into E. coli. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Mutagenesis can also be conducted using a QuikChange multisite-directed mutagenesis kit (Stratagene) and the like. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) or strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutated protein). The set of cleavage fragments is fractionated by, for example, HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

V. PmPpA Enzyme

Inorganic pyrophosphatase (PpA) is a member if the Ppase family (EC 3.6.1.1 inorganic diphosphatase). PpA is an enzyme that catalyzes the conversion of one molecule of inorganic pyrophosphate (PPi) to two phosphate ions (2Pi). PpAs have been sequenced from bacteria such as *Escherichia coli* (homohexamer), *Bacillus* PS3 (Thermophilic bacterium PS-3), *Pasteurella multocida* and *Thermus thermophilus*, from the archaebacteria *Thermoplasma acidophilum*, from fungi (homodimer), from plants (*Oryza sativa* subsp. *japonica* and *Arabidopsis thaliana*) and from bovine retina. In yeast (*Saccharomyces cerevisiae* and *Schizosaccharomyces pombe*), a mitochondrial isoform of PpA has been characterized. The sequences of PpAs share regions of similarities, among which is a region that contains three conserved aspartates that are involved in the binding of cations. Accordingly, representative PpAs of the instant invention include, but are not limited to, PpAs of family EC 3.6.1.1. In one embodiment, PmPpA from *Pasteurella multocida* is a preferred PmPpA of the invention (sec, Lau K, Thon V, Yu H, Ding L, Chen Y, Muthana M M, Wong D, Huang R, and Chen X. Chem. Commun. 2010, 46, 6066-6068).

The Pm PpAs of the present invention can include a polypeptide having any suitable percent identity to a reference sequence (e.g., SEQ ID NO:3). For example, the PmPpA of the present invention can include a polypeptide having a percent sequence identity to SEQ ID NO:3 of at least 20, 30, 40, 50, 55, 60, 65, 70, 75, 80, 85, 90, 91, 92, 93, 94, 95, 96, 97, 98 or at least 99%. In some embodiments, percent sequence identity can be at least 80%. In some embodiments, percent sequence identity can be at least 90%. In some embodiments, percent sequence identity can be at least 95%. In some embodiments, the PpA has a sequence identity of at least about 90%, 91%, 92%, 93%, 94%, 95%, 96%, 97%, 98% or 99%, or is identical to SEQ ID NO: 3. In some embodiments, the invention provides an isolated or purified polypeptide including an amino acid sequence selected from SEQ ID NO:3 (PmPpA-His$_6$, His tag is underlined).

The precise length of the PmPpA can vary, and certain variants can be advantageous for expression and purification of the enzymes with high yields. For example, removal of certain peptide subunits from the overall polypeptide sequence of a PmPpA can improve solubility of the enzyme and increase expression levels. Alternatively, addition of certain peptide or protein subunits to a PmPp A polypeptide sequence can modulate expression, solubility, activity, or other properties. The PmPpA's of the present invention can include point mutations at any position of the PmPpA sequence (i.e., SEQ ID NO:3) or a PmPpA variant (e.g., a fusion protein or a truncated form). The mutants can include any suitable amino acid other than the native amino acid. For example, the amino acid can be V, I, L, M, F, W, P, S, T, A, G, C, Y, N, Q, D, E, K, R, or H. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention.

The PmPpAs of the present invention can be constructed by mutating the DNA sequences that encode the corresponding unmodified PmPpA (e.g., a wild-type PmPpA such as SEQ ID NO:5 or a corresponding variant), such as by using techniques commonly referred to as site-directed mutagenesis. Nucleic acid molecules encoding the unmodified form of the PmPpA can be mutated by a variety of techniques well-known to one of ordinary skill in the art. (See, e.g., PCR Strategies (M. A. Innis, D. H. Gelfand, and J. J. Sninsky eds., 1995, Academic Press, San Diego, Calif.) at Chapter 14; PCR Protocols: A Guide to Methods and Applications (M. A. Innis, D. H. Gelfand, J. J. Sninsky, and T. J. White eds., Academic Press, N Y, 1990).

By way of non-limiting example, the two primer system, utilized in the Transformer Site-Directed Mutagenesis kit from Clontech, may be employed for introducing site-directed mutants into a polynucleotide encoding an unmodified form of the PmPpA. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Mutagenesis can also be conducted using a QuikChange multisite-directed mutagenesis kit (Stratagene) and the like. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) or strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutated protein). The set of cleavage fragments is fractionated by, for example, HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

Recombinant Nucleic Acids

Fucosyltransferase variants, PpA variants, and BfFKP variants, can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified fucosyltransferase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (Anal. Biochem. 324:285-291. 2004) may be utilized.

Accordingly, also provided are recombinant nucleic acids, optionally isolated, encoding any of the fucosyltransferases of the present invention. In some embodiments, the invention provides an isolated or purified polynucleotide including a nucleotide sequence that is substantially identical to, and encodes for the amino acid sequence of SEQ ID NO:1 (Te2FT), His$_6$-Te2FT, and MBP-Te2FT-His$_6$, or complements thereof. In some embodiments, the polynucleotide includes a nucleotide sequence that is substantially identical to, and encodes for the amino acid of SEQ ID NO:1 (Te2FT), His$_6$-Te2FT, and MBP-Te2FT-His$_6$, or complements thereof. In general, the polynucleotide has at least 50% sequence identity to the corresponding nucleotide sequence that encodes for amino acid sequence SEQ ID NO:1. The sequence identity can be, for example, 50%, 55%, 60%, 65%, 70%, 75%, 80%, 85%, 90%, 91%, 92%, 93%, 94%, 95%, 96%, 97%, 98%, 99%, or 100%. In some embodiments, a given polynucleotide can be optimized for expression in yeast.

The instant invention also provides recombinant nucleic acids, optionally isolated, encoding any of the PpA's of the present invention. In some embodiments, the invention provides an isolated or purified polynucleotide including a nucleotide sequence that is substantially identical to SEQ ID NO:5 (PmPpA) or complements thereof. In some embodiments, the polynucleotide includes a nucleotide sequence that is substantially identical to SEQ ID NO:5 (PmPpA), or compliments thereof. In general, the polynucleotide has at least 50% sequence identity to SEQ ID NO:5. The sequence identity can be, for example, 50%, 55%, 60%, 65%, 70%, 75%, 80%, 85%, 90%, 91%, 92%, 93%, 94%, 95%, 96%, 97%, 98%, 99%, Or 100%. In some embodiments, a given polynucleotide can be optimized for expression in yeast. In some embodiments, the polynucleotide contains a sequence comprising SEQ ID NO:5 (in the absence of the nucleotide sequence corresponding to the his-tag), and complements thereof.

Also provided are recombinant nucleic acids, optionally isolated, encoding any of the BftKP's of the present invention. In some embodiments, the invention provides an isolated or purified polynucleotide including a nucleotide sequence that is substantially identical to SEQ ID NO:4 (BfFKP) or complements thereof. In some embodiments, the polynucleotide includes a nucleotide sequence that is substantially identical to SEQ ID NO:4 (BfFKP), or complements thereof. In general, the polynucleotide has at least 50% sequence identity to SEQ ID NO:4. The sequence identity can be, for example, 50%, 55%, 60%, 65%, 70%, 75%, 80%, 85%, 90%, 91%, 92%, 93%, 94%, 95%, 96%, 97%, 98%, 99%, or 100%. In some embodiments, a given polynucleotide can be optimized for expression in yeast. In some embodiments, the polynucleotide contains a sequence comprising SEQ ID NO: 4 (in the absence of the nucleotide sequence corresponding to the his-tag), and complements thereof.

Using a nucleic acid of the present invention, encoding a fucosyltransferase of the invention, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant fucosyltransferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the fucosyltransferase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., E. coli) where a "heat-step" may be employed. The construction of suitable vectors containing DNA encoding replication sequences, regulatory sequences, phenotypic selection genes, and the mutant fucosyltransferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., Molecular Cloning: A Laboratory Manual (Cold Spring Harbor Laboratory Press, New York, N.Y., 2nd ed. 1989)). In some embodiments, the present invention provides a recombinant nucleic acid encoding an isolated fucosyltransferase of the present invention.

As discussed above, the present invention also features a vector, e.g., a vector containing a nucleic acid of the present invention, encoding a fucosyltransferase of the invention. The vector can further include one or more regulatory elements, e.g., a heterologous promoter. The regulatory elements can be operably linked to a gene encoding a protein, a gene construct encoding a fusion protein gene, or a series of genes linked in an operon in order to express the fusion protein. In yet another aspect, the invention comprises an isolated recombinant cell, e.g., a bacterial cell containing an aforementioned nucleic acid molecule or vector. The nucleic acid is optionally integrated into the genome.

Accordingly, the invention provides an expression cassette comprising a heterologous promoter operably linked to a nucleic acid encoding an α1-2-fucosyltransferase, wherein the α1-2-fucosyltransferase has a sequence identity of at least about 62% to SEQ ID NO:1. In some embodiments, the expression cassette comprises a α1-2-fucosyltransferase having a sequence identity of at least about 90%, 91%, 92%, 93%,₉₄%, 95%, 96%, 97%, 98%, or 99%, or is identical to SEQ ID NO:1 In some embodiments, the expression cassette comprises a α1-2-fucosyltransferase having high α1-2-fucosyltransferase activity and low donor hydrolysis activity. In some embodiments, the α1-2-fucosyltransferase comprises an enzyme having an α1-2-fucosyltransferase activity that is at least 2-fold, 3-fold, 4-fold, or 5-fold more than the α1-2-fucosyltransferase activity of GST-WbsJ, His₆Prop-WgbL, and Hp2FT, and wherein the α1-2-fucosyltransferase activity is measured as the $k_{cat}$ value for GDP-fucose.

Host Cells

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a fucosyltransferase of the invention is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include CaPO4 precipitation, liposome fusion, LIPOFECTIN®, electroporation, viral infection, and the like.

In some embodiments, prokaryotes are used as host cells for the initial cloning steps of the present invention. Other host cells include, but are not limited to, eukaryotic (e.g., mammalian, plant and insect cells), or prokaryotic (bacterial) cells. Exemplary host cells include, but are not limited to, Escherichia coli, Saccharomyces cerevisiae, Pichia pastoris, Sf9 insect cells, and CHO cells. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include E. coli K12 strain 94 (ATCC No. 31,446), E. coli strain W3110 (ATCC No. 27,325), E. coli K12 strain DG116 (ATCC No. 53,606), E. coli X1776 (ATCC No. 31,537), and E. coli B; however many other strains of E. coli, such as HB101, JM101, NM522, NM538, NM539, and many other species and genera of prokaryotes including bacilli such as Bacillus subtilis, other enterobacteriaceae such as Salmonella typhimuriun or Serratia marcesans, and various Pseudomonas species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in Genetic Engineering, Principles and Methods 12:275-296 (Plenum Publishing Corp., 1990); Hanahan et al., Meth. Enzymol., 204:63, 1991. Plasmids typically used for transformation of E. coli include pBR322, pUCI8, pUCI9, pUC118, pUC119, and Bluescript M13, all of which are described in sections 1.12-1.20 of Sambrook et al., supra. However, many other suitable vectors are available as well.

In some embodiments, the fucosyltransferases of the present invention are produced by culturing a host cell transformed with an expression vector containing a nucleic acid encoding the fucosyltransferase, under the appropriate conditions to induce or cause expression of the fucosyltransferase. Methods of culturing transformed host cells under conditions suitable for protein expression are well-known in the art (see, e.g., Sambrook et al., supra).

In some embodiments, a suitable production host bacterial strain is one that is not the same bacterial strain as the source bacterial strain from which the fucosyltransferase-encoding nucleic acid sequence was identified. For example, the bacterium may comprise an exogenous α1-2-fucosyltransferase gene. Exemplary α1-2-fucosyltransferase genes include *Escherichia coli* O126 wbgL, *Helicobacter mustelae* 12198 (ATCC 43772) α1-2-fucosyltransferase (futL), and *Bacteroides vulgatus* ATCC 8482 glycosyl transferase family protein (futN). In one embodiment, an exogenous α1-2-fucosyltransferase gene is selected from the group consisting of *Escherichia coli* O126 wbgL, *Helicobacter mustelae* 12198 (ATCC 43772) α1-2-fucosyltransferase (futL), *Bacteroides vulgatus* ATCC 8482 glycosyl transferase family protein (futN), *Bacteroides fragilis* (NCTC) 9343 fucosyl transferase (bft3/wcfB), *Escherichia coli* O55:H7 (str. CB9615) fucosyltransferase (wbgN), *Helicobacter bilis* ATCC 437879 futD, *Vibrio cholera* O22 wblA, *Bacteroides fragilis* (NCTC) 9343 α1-2-fucosyltransferase (bft1), *Bacteroides ovatus* ATCC 8483 futO, and *Helicobacter cinaedi* CCUG 18818 α1-2-fucosyltransferase (futE). In certain embodiments, it is preferable that the exogenous α1-2-fucosyltransferase gene comprises at least 62% to SEQ ID NO: 1.

In some embodiments, the exogenous α1-2-fucosyltransferase gene comprises *Helicobacter pylori* 26695 alpha-(1-2)fucosyltransferase (futC), e.g., at least 15%, at least 20%, at least 25%, at least 30% identity. In some embodiments, the exogenous α1-2-fucosyltransferase gene comprises (futL), e.g., at least 15%, at least 20%, at least 25%, at least 30% identity. FutL is 70% identical to FutC at the amino acid level.

Accordingly, the invention provides a host cell comprising an expression cassette comprising a heterologous promoter operably linked to a nucleic acid encoding an α1-2-fucosyltransferase, wherein the α1-2-fucosyltransferase has a sequence identity of at least about 62% to SEQ ID NO:1. In some embodiments, the host cell comprising the expression cassette includes a α1-2-fucosyltransferase having a sequence identity of at least about 90%, 91%, 92%, 93%, 94%, 95%, 96%, 97%, 98%, or 99%, or is identical to SEQ ID NO:1 In some embodiments, the host cell comprising the expression cassette includes a α1-2-fucosyltransferase having high α1-2-fucosyltransferase activity and low donor hydrolysis activity. In some embodiments, the host cell comprising the expression cassette having a α1-2-fucosyltransferase includes α1-2-fucosyltransferase activity that is at least 2-fold, 3-fold, 4-fold, or 5-fold more than the α1-2-fucosyltransferase activity of GST-WbsJ, His$_6$Prop-WgbL, and Hp2FT, and wherein the α1-2-fucosyltransferase activity is measured as the $k_{cat}$ value for GDP-fucose.

Following expression, the fucosyltransferase can be harvested and isolated. Methods for purifying thermostable glycosyltransferases are described in, for example, Lawyer et al., supra. In some embodiments, the present invention provides a cell including a recombinant nucleic acid of the present invention. In some embodiments, the cell can be prokaryotes, eukaryotes, mammalian, plant, bacteria or insect cells.

VI. Methods of Making Oligosaccharides

The fucosyltransferases of the present invention can be used to prepare glycoconjugates, specifically to add fucose and analogs thereof, to an acceptor substrate, such as a galactose (Gal), or N-acetylglucosamine (GlcNAc). For example, Te2FT can catalyze the addition of fucose to form α1-2-fucosides, such as β1-3-linked galactose (Gal) or N-acetylglucosamine (GlcNAc) glycoconjugates.

Accordingly, some embodiments of the present invention provide a method of preparing α1-2 fucosides. The method includes forming a reaction mixture containing an acceptor substrate, a donor substrate having a sugar moiety and a nucleotide, and a fucosyltransferase of the present invention. The fucosyltransferase includes a polypeptide having a sequence that is selected from SEQ ID NO:1 (Te2FT), (Te2FT-His$_6$), and (MBP-Te2FT-His$_6$). The reaction mixture is formed under conditions sufficient to transfer the sugar moiety from the donor substrate to the acceptor substrate, thereby forming the α1-2 fucoside.

In one embodiment, the reaction mixture comprises an α1-2-fucosyltransferase enzyme having a sequence identity of at least about 62% to the α1-2-fucosyltransferase of SEQ ID NO:1 (Te2FT) and a bifunctional L-fucokinase/GDP-fucose pyrophosphorylase enzyme, or a inorganic pyrophosphatase enzyme, or the combination thereof. In some embodiments, the α1-2-fucosyltransferase in the reaction mixture has a sequence identity of at least about 90%, 91%, 92%, 93%, 94%, 95%, 96%, 97%, 98%, or 99%, or is identical to SEQ ID NO:1. In some embodiments, the α1-2-fucosyltransferase is heterologous with respect to the bifunctional L-fucokinase/GDP-fucose pyrophosphorylase enzyme or inorganic pyrophosphatase enzyme. In some embodiments, the reaction mixture comprises an α1-2-fucosyltransferase enzyme, a bifunctional L-fucokinase/GDP-fucose pyrophosphorylase enzyme, and a inorganic pyrophosphatase enzyme. In one embodiment, the bifunctional L-fucokinase/GDP-fucose pyrophosphorylase enzyme is BfFKP from *Bacteriodes fragilis* strain NCTC9343. In some embodiments, the bifunctional L-fucokinase/GDP-fucose pyrophosphorylase has a sequence identity of at least about 90%, 91%, 92%, 93%, 94%, 95%, 96%, 97%, 98%, or 99%, or is identical to SEQ ID NO:2. In one embodiment, the inorganic pyrophosphatase enzyme is PmPpA from *Pasteurella multocida*. In some embodiments, the inorganic pyrophosphatase has a sequence identity of at least about 90%, 91%, 92%, 93%, 94%, 95%, 96%, 97%, 98%, or 99%, or is identical to SEQ ID NO:3. In some embodiments, the reaction mixture further comprises guanidine 5'-diphosphate-fucose (GDP-Fucose). In some embodiments, the reaction mixture further comprises Galβ1-3GlcNAcβ2AA, Galβ1-4GlcNAcβ2AA, or Galβ1-4Glcβ2AA. In this context, 2AA refers to anthranilic acid (2-aminobenzoic acid). In some embodiments, the reaction mixture further comprises Galβ1-3GlcNAcβOR, Galβ1-3GlcNAcαOR, Galβ1-3GalNAcαOR, or Galβ1-3GalNAcβOR, wherein R is selected from OH, OCH$_2$CH$_2$CH$_2$N$_3$ or lactose. In some embodiments, the reaction mixture further comprises Galβ1-3GalNAcαProN$_3$, Galβ1-3GalNAcβProN$_3$, Galβ1-3GlcNAcαProN$_3$, Galβ1-3GlcNAcβProN$_3$ or lacto-N-tetraose. In some embodiments, the invention provides a method of making an α1-2-linked fucoside, the method comprising providing a reaction mixture as described in the preceding paragraph, wherein the reaction mixture further comprises an acceptor and incubating the reaction mixture under conditions suitable to form the α1-2-linked fucoside. In some embodiments, the acceptor is a β1-3 acceptor selected from the group consisting of Galβ1-3GlcNAcβProN₃, Galβ1-3GlcNAcαProN₃, Galβ1-3GalNAcβProN₃, or Galβ1-3GalNAcαProN₃. In some embodiments, the acceptor is lacto-N-tetraose. In some embodiments, the α1-2-linked fucoside is a human blood group H antigen or lacto-N-fucopentaose I. In some embodiments, the α1-2-linked fucoside is a α1-2-fucosylated 31-3 linked galactoside. In some embodiments, the α1-2-linked fucoside is selected from the group consisting of Fucα1-2Galβ1-3GlcNAcβProN₃, Fucα1-2Galβ1-3GlcNAcαProN₃, Fucα1-2Galβ1-3GalNAcβProN₃, and Fucα1-2Galβ1-3GalNAcαProN₃. In one embodiment, the α1-2-linked fucoside is lacto-N-fucopentaose I.

Any suitable acceptor glycoconjugate can be used in the methods of the invention. In some embodiments, the acceptor glycoconjugate comprises a galactoside moiety. In some embodiments, the galactoside moiety is selected from the group consisting of a β1-4-linked galactoside moiety and a β1-3-linked galactoside moiety. In some embodiments, the acceptor glycoconjugate comprises a Galβ1-3GlcNAc moiety or a Galβ1-3GalNAc moiety.

The donor substrate of the present invention includes a nucleotide and sugar. Suitable nucleotides include, but are not limited to, adenine, guanine, cytosine, uracil and thymine nucleotides with one, two or three phosphate groups. In some embodiments, the nucleotide can be GTP.

The methods of the invention include providing reaction mixtures that contain the α1-2-fucosyltransferases described herein. The α1-2-fucosyltransferases can be, for example, purified prior to addition to the reaction mixture or secreted by a cell present in the reaction mixture. Alternatively, an α1-2-fucosyltransferase can catalyze the reaction within a cell expressing the α1-2-fucosyltransferase Optionally, α1-2-fucosyltransferases secreted by a host cell can be isolated from the host cell or the spent media.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, CaCl2, and salts of $Mn^{2+}$ and $Mg^{2+}$), chelators (e.g., ethylene glycol-bis(2-aminoethylether)-N,N,N,N-tetraacetic acid (EGTA), 2-({2-[Bis(carboxymethyl)amino]ethyl}(carboxymethyl)amino)acetic acid (EDTA), and 1,2-bis(o-aminophenoxy)ethane-N,N,N,N-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, chelators, reducing agents, and labels can be used at any suitable concentration, which can be readily determined by one of skill in the art. In general, buffers, cosolvents, salts, chelators, reducing agents, and labels are included in reaction mixtures at concentrations ranging from about 1 μM to about 1 M. For example, a buffer, a cosolvent, a salt, a chelator, a reducing agent, or a label can be included in a reaction mixture at a concentration of about 1 μM, or about 10 μM, or about 100 μM, or about 1 μM, or about 10 mM, or about 25 μM, or about 50 mM, or about 100 mM, or about 250 n M, or about 500 mM, or about 1 M.

Reactions are conducted under conditions sufficient to transfer the sugar moiety from a donor substrate to an acceptor substrate. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of a particular fucosyltransferase, donor substrate, or acceptor molecule.

VII. Examples

General Materials And Methods

Chemicals and Reagents

Chemicals were purchased and used without further purification. $^1$H NMR (800 MHz) and $^{13}$C NMR (200 MHz) spectra were recorded on a Bruker Avance-800 NMR spectrometer. High resolution electrospray ionization (ESI) mass spectra were obtained using Thermo Electron LTQ-Orbitrap Hybrid MS at the Mass Spectrometry Facility in the University of California, Davis. Silica gel 60 Å (230-400 mesh, Sorbent Technologies) was used for flash column chromatography. Thin-layer chromatography (TLC, Sorbent Technologies) was performed on silica gel plates using anisaldehyde sugar stain or 5% sulfuric acid in ethanol stain for detection. Gel filtration chromatography was performed with a column (100 cm×2.5 cm) packed with Bio-Gel P-2 Fine resins (Bio-Rad, Hercules, Calif., USA). D-Lactose, D-galactose, and N-acetyl-D-glucosamine (D-GlcNAc) were from Fisher Scientific (Pittsburgh, Pa., USA). L-Fucose was from V-LABS (Covington, La., USA). Lacto-N-tetraose (LNT) was from Elicityl (Crolles, France). Guanidine 5'-triphosphate (GTP) was from Hangzhou Meiya Pharmacy (Hangzhou, China). Adenosine 5'-triphosphate (ATP) was from Beta Pharma Scientific, Inc. (Branford, Connectic, USA). Recombinant enzymes *Bacteroides fragilis* strain NCTC9343 bifunctional L-fucokinase/GDP-fucose pyrophosphorylase (FKP)[24] and *Pasteurella multocida* inorganic pyrophosphatase (PmPpA)[25] were expressed and purified as described previously. Compounds Galβ1-3GalNAcαProN₃, Galβ1-3GalNAcβProN₃, Galβ1-3GlcNAcαProN₃, Galβ1-3GlcNAcβProN₃ were synthesized as described previously.[34]

Bacterial Strains, Plasmids, And Materials

Electrocompetent *Escherichia coli* cells DH5a and chemically competent cells BL21 (DE3) were from Invitrogen (Carlsbad, Calif., USA). Vector plasmids pET15b and pMAL-c4X were purchased from Novagen (EMD Biosciences Inc., Madison, Wis., USA). QIAprep spin miniprep kit and QIAquick gel extraction kit were from Qiagen (Valencia, Calif., USA). Herculase-enhanced DNA polymerase was from Stratagene (La Jolla, Calif., USA). T4 DNA ligase and 1 kb DNA ladder were from Promega (Madison, Wis., USA). NdeI, BamHI, EcoRI, and SalI restriction enzymes, Taq 2× Master Mix, and amylose resin were from New England Biolabs (Beverly, Mass., USA). Nickel-nitrilotriacetic acid agarose ($Ni^{2+}$-NTA agarose) was from 5 PRIME (Gaithersburg, Md., USA).

Example 1

Cloning, Expression, And Purification of $His_6$-Te2FT And MBP-Te2FT-$His_6$

Methods

Cloning

Full-length synthetic gene for Te2FT with codons optimized for E. coli expression was customer synthesized by Biomatik (Wilmington, Del., USA) and provided in a pBSK (+) vector. The primers used for cloning $His_6$-Te2FT in to pET15b vector were: forward primer 5'-GATC CATATGATTATCGTTCACCTGTGCG-3' (NdeI restriction site is underlined) (SEQ ID NO:6) and reverse primer 5'-AAGGGATCCTTACAGAACAATCCAACCC-3' (BamHI restriction site is underlined) (SEQ ID NO:7). The primers used for cloning the MBP-Te2FT-$His_6$ in to pMAL-c4X vector were: forward primer 5'-GATC CATATGGTGAAAGTACTGACTGTATT-3' (EcoRI restriction site is underlined) (SEQ ID NO:8) and reverse primer 5'-ACGCGTCGACTTAGTGGTGGTGGTGG-TGGTGCAGAACAATCCAACCC-3' (SalI restriction site is underlined) (SEQ ID NO:9).

Polymerase chain reactions (PCRs) for amplifying the target gene were performed in a 50 μL reaction mixture containing plasmid DNA (10 ng), forward and reverse primers (0.2 μM each), Taq 2× Master Mix. The PCR procedure included an initial cycle of 30 seconds at 95° C., followed by 30 cycles of 30 seconds at 95° C., 30 seconds at 56° C., and 1 minute at 68° C. For the final extension, the reaction was held at 68° C. for 10 minutes. The resulting PCR product was purified and double digested with NdeI and BamHI or EcoRI and SalI restriction enzymes. The purified and digested PCR products were ligated with the predigested pET15b vector or pMAL-c4X and transformed into electrocompetent E. coli DH5a cells.

Expression And Purification of MBP-Te2FT-$His_6$

Positive plasmids were selected and transformed into E. coli BL21 (DE3) chemical competent cells. The plasmid-bearing E. coli strains were cultured in LB medium (10 g $L^{-1}$ tryptone, 5 g $L^{-1}$ yeast extract, and 10 g $L^{-1}$ NaCl) supplemented with ampicillin (100 μg $mL^{-1}$). Overexpression of the target protein was achieved by inducing the E. coli culture with 0.1 mM of isopropyl-1-thio-β-D-galactopyranoside (IPTG) when $OD_{600\ nm}$ reached 0.6-0.8 followed by incubating at 16° C. for 20 hours with shaking at 160 rpm in a C25KC incubator shaker (New Brunswick Scientific, Edison, N.J.).

$His_6$-tagged target proteins were purified from cell lysate. To obtain the cell lysate, cell pellet harvested by centrifugation at 4000 rpm for 1 h was resuspended (30 mL $L^{-1}$ cell culture) in lysis buffer (pH 8.0, 100 mM Tris-HCl containing 0.1% TRITON X-100®). The sonication protocol was 2 seconds (sonication)/3 seconds (rest) for a total of 7 min on ice. Cell lysate was obtained by centrifugation at 11,000 rpm for 25 min as the supernatant. Purification of $His_6$-tagged proteins from the lysate was achieved using a $Ni^{2+}$-resin column. The column was pre-equilibrated with 10 column volumes of binding buffer (5 mM imidazole, 0.5 M NaCl, 50 mM Tris-HCl, pH 7.5) before the lysate was loaded. After washing with 8 column volumes of binding buffer and 10 column volumes of washing buffer (50 mM imidazole, 0.5 M NaCl, 50 mM Tris-HCl, pH 7.5), the protein was eluted with an elute buffer (200 mM imidazole, 0.5 M NaCl, 50 mM Tris-HCl, pH 7.5).

Sodium Dodecylsulfate-Polyacrylamide Gel Electrophoresis (SDS-PAGE) of $His_6$-Te2FT And MBP-Te2FT-$His_6$ SDS-PAGE was performed in a 12% Tris-glycine gel using a Bio-Rad Mini-protein III cell gel electrophoresis unit (Bio-Rad, Hercules, Calif.) at DC=125 V. Bio-Rad Precision Plus Protein Standards (10-250 kDa) were used as molecular weight standards. Gels were stained with Coomassie Blue.

Quantification of Purified Protein

The purified proteins were quantified in a 96-well plate using a Bicinchoninic acid (BCA) Protein Assay Kit (Pierce Biotechnology, Rockford, Ill.) with bovine serum albumin as a protein standard. The absorbance of samples was measured at 562 nm by a BioTek Synergy™ HT Multi-Mode Microplate Reader.

Protein Encoded by the Gene T110994 from Thermophilic cyanobacterium Thermosynechococcus Elongatus BP-1

Protein encoded by tll0994 gene from thermophilic cyanobacterium Thermosynechococcus elongatus BP-11[16], designated as Te2FT, was identified by BLAST search as a hypothetic α1-2-fucosyltransferase due to its sequence homology to a α1-2-fucosyltransferase from E. coli O86:B7 WbwK. The EMBOSS Needle alignment tool (www.ebi.ac.uk/bwK5Tools/psa/emboss_needle/) was used for protein sequence alignment. As shown in FIG. 1, the hypothetical α1-2-fucosyltransferase encoded in cyanobacterium T. elongatus BP-1 genome (Te2FT) shares 32.3% identity and 48.3% similarity to E. coli O86:B7 WbwK belonging to Carbohydrate Active Enzyme (CAZy) glycosyltransferase family 11 (GT 11) that is involved in the biosynthesis of lipopolysaccharide (O-antigen) of the bacterium.[13a] It also shares 32% identity to E. coli O128:B12 WbgL that has been used for the synthesis of 2'-fucosyllactose.[15a] The sequence alignment shows that Te2FT shares 27-33% identities and 44-48% similarities to the previously reported α1-2-fucosyltransferases of FIG. 1 which contains all α1-2-fucosyltransferases characterized to date with except for Dictyostelium discoideum which is a bifunctional β3GalT and α2FT in the CAZy GT74 family.[18] The sequence alignment also indicates Te2FT has four conserved motifs (I-IV) shared by GT11 family fucosyltransferases including highly conserved motif I ($H^{162}xR^{164}R^{165}xD^{167}$) which is likely involved in GDP-fucose binding.[13b] Residues $R^{164}$ and $D^{167}$ were indicated to play critical roles in donor binding and enzyme activity.[13b] FIG. 1 shows the amino acid sequence alignment of Te2FT (UniProtKB:Q8DK72, GenBank: BAC08546.1), H. pylori FutC (UniProtKB:A4L7J1), E. coli O127:K63 WbiQ (UniProtKB:Q5J7C6), E. coli O86:K62:H2 WbnK (UniProtKB:Q58YV9), E. coli O128:B12 WbsJ (UniProtKB:Q6XQ53), E. coli O86:B7 WbwK (GenBank:AAO37719.1), and E. coli O126 WbgL (UniProtKB: A6M9C2).

Expression and Purification of of $His_6$-Te2FT And MBP-Te2FT-$His_6$

Te2FT was cloned as an N-$His_6$-tagged recombinant protein ($His_6$-Te2FT) in pET15b vector, as well as an N-MBP-fused and C-$His_6$-tagged recombinant protein (MBP-Te2FT-$His_6$) in pMAL-c4X vector. $Ni^{2+}$-column purified proteins were found to have molecular weights close to the calculated value of 36.2 KDa ($His_6$-Te2FT) and 75.8 KDa (MBP-Te2FT-$His_6$), respectively (FIG. 2). When expressed at optimal conditions at 16° C. for 20 hours with shaking at 120 rpm, the expression levels of $His_6$-Te2FT and MBP-Te2FT-$His_6$ were 15 and 16 mg per liter, respectively. The expression level of $His_6$-Te2FT (15 mg/L culture) was significantly higher than other reported α1-2FTs[15a] and was comparable to recombinant C-truncated *Helicobacter pylori* α3FT[19] which, partially due to its easy accessibility by recombinant 5 expression, has been crystallized[20] and broadly used in enzymatic and chemoenzymatic synthesis of α1-3-linked fucosides.[21] Due to its good expression level and lower molecular weight compared to MBP-Te2FT-$His_6$, $His_6$-Te2FT was used for more detailed characterization and synthesis.

Example 2 pH Profiles of $His_6$-Te2FT

Methods ph Profile of α1-2-Fucosyltransferase Activity of $His_6$-Te2FT By High-Performance Liquid Chromatography (HPLC)

Each reaction was carried out in duplicate at 37° C. for 10 minutes in a total volume of 10 μL in a buffer (200 mM) with pH varying from 3.0 to 11.0. The buffers used were: Citric, pH 3.0-4.0, NaOAc/HOAc, pH 4.5, MES, pH 5.0-6.5; Tris-HCl, pH 7.0-9.0; and CAPS, pH 10.0-11.0. The reaction system was: GDP-fucose (1 mM), fluorophore 2-anthranilic acid (2AA)-labeled oligosaccharide (Galβ1-3GlcNAcβ2AA, 1 mM), $MgCl_2$ (20 mM), and the recombinant enzyme, $His_6$-Te2FT (0.25 μg). The reaction mixture was stopped by boiling for 2 min and then adding an equal volume of water (10 μL) to make a ten-fold dilution for Galβ1-3GlcNAcβ2AA. The samples were analyzed by a Shimadzu LC-2010A system equipped with a membrane online degasser, a temperature control unit and a fluorescence detector. A reverse-phase Premier C18 column (250× 4.6 mm i.d., 5 μm particle size, Shimadzu) protected with a C18 guard column cartridge was used. The mobile phase was 20% acetonitrile. The ratio of the absorbance for fluorescent-labeled product at 315-400 nm was determined.

Results

Figure 4:
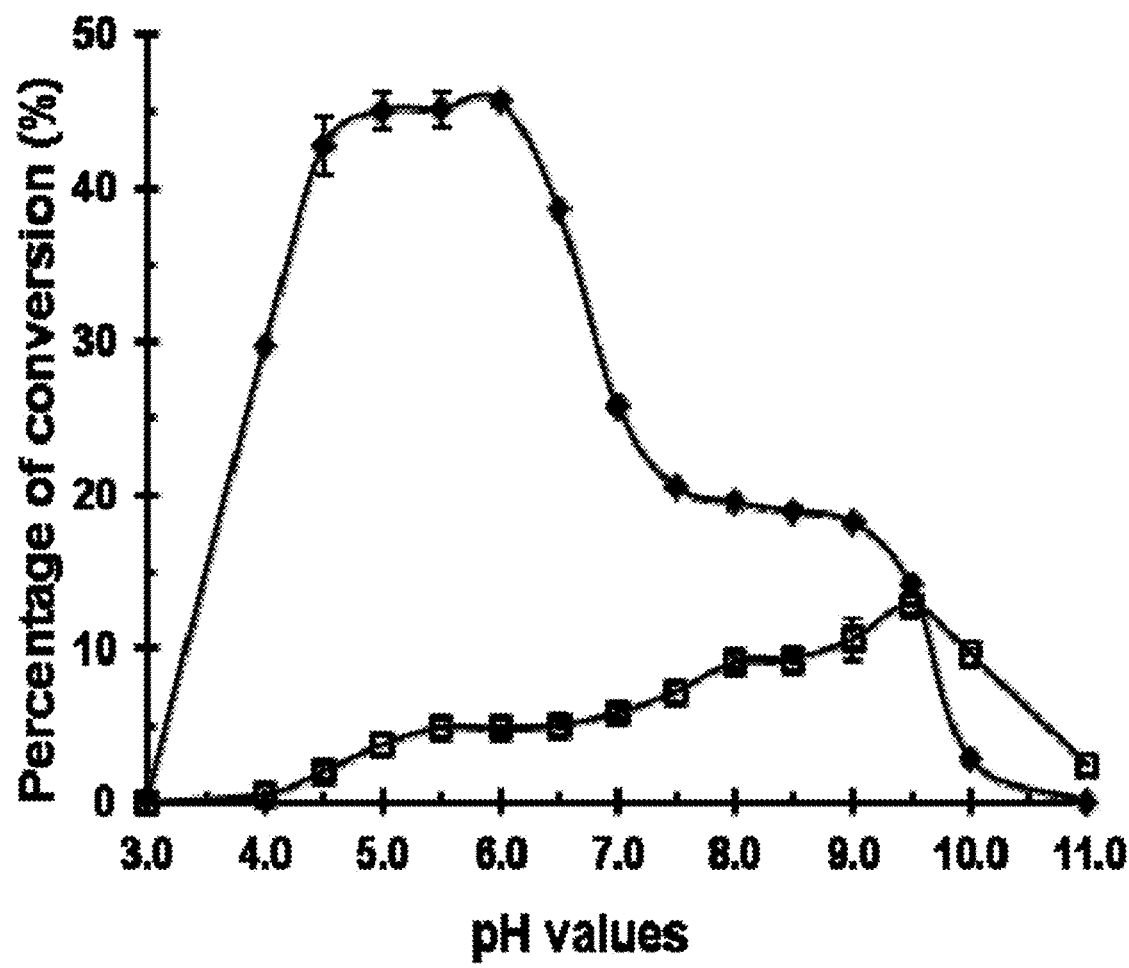
FIG. 4 shows the pH profiles of the α1-2-fucosyltransferase activity (filled diamond, Galβ1-3GlcNAcβ2AA was used as an acceptor substrate) and the GDP-fucose hydrolysis activity (open square) of His$_6$-Te2FT. In this assay, 15-fold more enzyme and 3-fold longer incubation time were used in the GDP-fucose hydrolysis activity assays than in the α1-2-fucosyltransferase activity assays. Buffers used: Citric, pH 3.0-4.0; NaOAc/HOAc, pH 4.5; MES, pH 5.0-6.0; Tris-HCl, pH 7.0-9.0; N-cyclohexyl-3-aminopropanesulfonic acid (CAPS), pH 10.0-11.0.

High performance liquid chromatography (HPLC)-based pH profile study using Galβ1-3GlcNAcβ2AA (a type I glycan with a fluorescent 2-anthranilic acid aglycone) as an acceptor showed that $His_6$-Te2FT was active in a broad pH range of 4.0-10.0 with optimal activities at pH 4.5-6.0 (FIG. 4). About 85% of the optimal activity was found at pH 6.5 under the experimental conditions used.

ph Profile of GDP-Fucose Hydrolysis of $His_6$-Te2FT By Capillary Electrophoresis Assays Each reaction was carried out in duplicate at 37° C. for 30 minutes in a total volume of 10 μL in a buffer (200 mM) with pH varying from 3.0 to 11.0. The buffers used were: Citric, pH 3.0-4.0, NaOAc/HOAc, pH 4.5, MES, pH 5.0-6.5; Tris-HCl, pH 7.0-9.0; and CAPS, pH 10.0-11.0 containing GDP-fucose (1 mM), $MgCl_2$ (20 mM) and the recombinant enzyme (3.75 μg). Reactions were stopped by boiling for 2 min followed by adding an equal volume of water (10 μL) to make a two-fold dilution. The samples were kept on ice until aliquots of 6 μL were withdrawn and analyzed by a Beckman P/ACE MDQ capillary electrophoresis system (60 cm×75 μm i.d.) with a PDA detector. The ratio of the absorbance for GDP-fucose and GDP at 254 nm was determined at different concentrations (2.5, 5, and 10 mM). All assays were carried out in duplicate.

Results

Guanosine 5'-diphosphate-fucose (GDP-fucose, a donor substrate for fucosyltransferases) hydrolysis activity of fucosyltransferases could lower synthetic yields,[23] to determine the effect of donor hydrolysis activity, an assay using $His_6$-Te2FT was carried out. To our surprise, using 15-fold more enzyme and 3-fold longer reaction time than those in the α1-2-fucosyltransferase activity assays (described above) indicated that the donor hydrolysis activity of $His_6$-Te2FT was at a minimum in the pH range (5.0-8.0) that would normally be used for the α1-2-fucosyltransfer reactions (FIG. 4). An optimal pH of 9.5 was observed for the GDP-fucose hydrolysis activity.

Example 3

Effects of Metal Ions, Dithiothreitol (DTT) And Ethylenediaminetetraacetic Acid (EDTA)

Methods

For metal effects, various concentrations (5 mM, 10 mM, or 20 mM) of $MgCl_2$ or $MnCl_2$ were added and EDTA (as a chelating agent) (10 mM) and DTT (10 mM) were used in a Tris-HCl buffer (pH 7.5, 200 mM) to analyze their effects on the α1-2-fucosyltransferase activity of $His_6$-Te2FT for acceptor Galβ1-3GlcNAcβ2AA. Reaction without metal ions, EDTA and DTT was used as a control. The effects of metal ions $Mg^{2+}$ and $Mn^{2+}$ as well as DTT and the chelating agent EDTA on the α1-2-fucosyltransferase activity of $His_6$-Te2FT toward and acceptor Galβ1-3GlcNAcβ2AA were examined at pH 7.5.

Results

Figure 5:
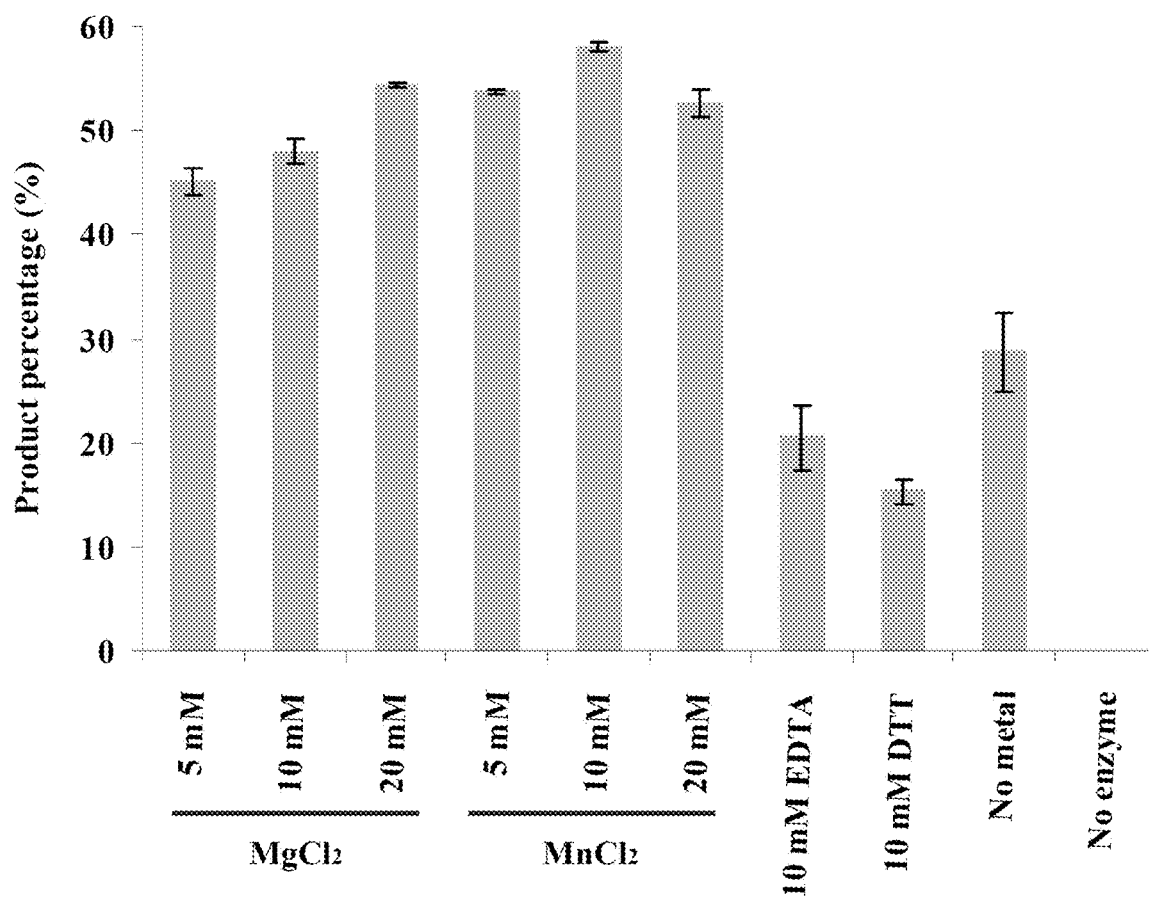
FIG. 5 shows the effects of divalent metal concentrations (Mg$^{2+}$ and Mn$^{2+}$), EDTA and and DTT (in the presence of 20 mM Mg$^{2+}$) on the fucosyltransferase activity of His$_6$-Te2FT when Galβ1-3GlcNAcβ2AA was used as an acceptor substrate.

A divalent metal ion was not required for the α1-2-fucosyltransferase activity of $His_6$-Te2FT. Adding 10 mM of ethylenediaminetetraacetic acid (EDTA) decreased its activity only slightly (FIG. 5). However, its activity was enhanced by about two-fold when 5-20 mM of $Mg^{2+}$ or $Mn^{2+}$ was added. The addition of 10 mM of dithiothreitol (DTT) decreased $His_6$-Te2FT activity moderately, indicating disulfide bond formation was not essential for the enzyme activity despite of the presence of 5 cysteine residues in the Te2FT protein sequence.

Example 4

Effect of Temperature on α1-2-Fucosyltransferase Activity of $His_6$-Te2FT

Methods

Assays were carried out in a total volume of 10 μL in a Tris-HCl buffer (pH 6.0, 200 mM) at temperatures ranging from 15° C. to 70° C. The reaction mixture contained GDP-fucose (1 mM), $MgCl_2$ (20 mM), Galβ1-3GlcNAcβ2AA (1 mM), and the recombinant $His_6$-Te2FT (1.5 μg). All reactions were allowed to proceed for 10 minutes at various temperatures. The reaction was stopped by boiling for 2 minutes, and diluted 60-fold for detection.

Results

Figure 6:
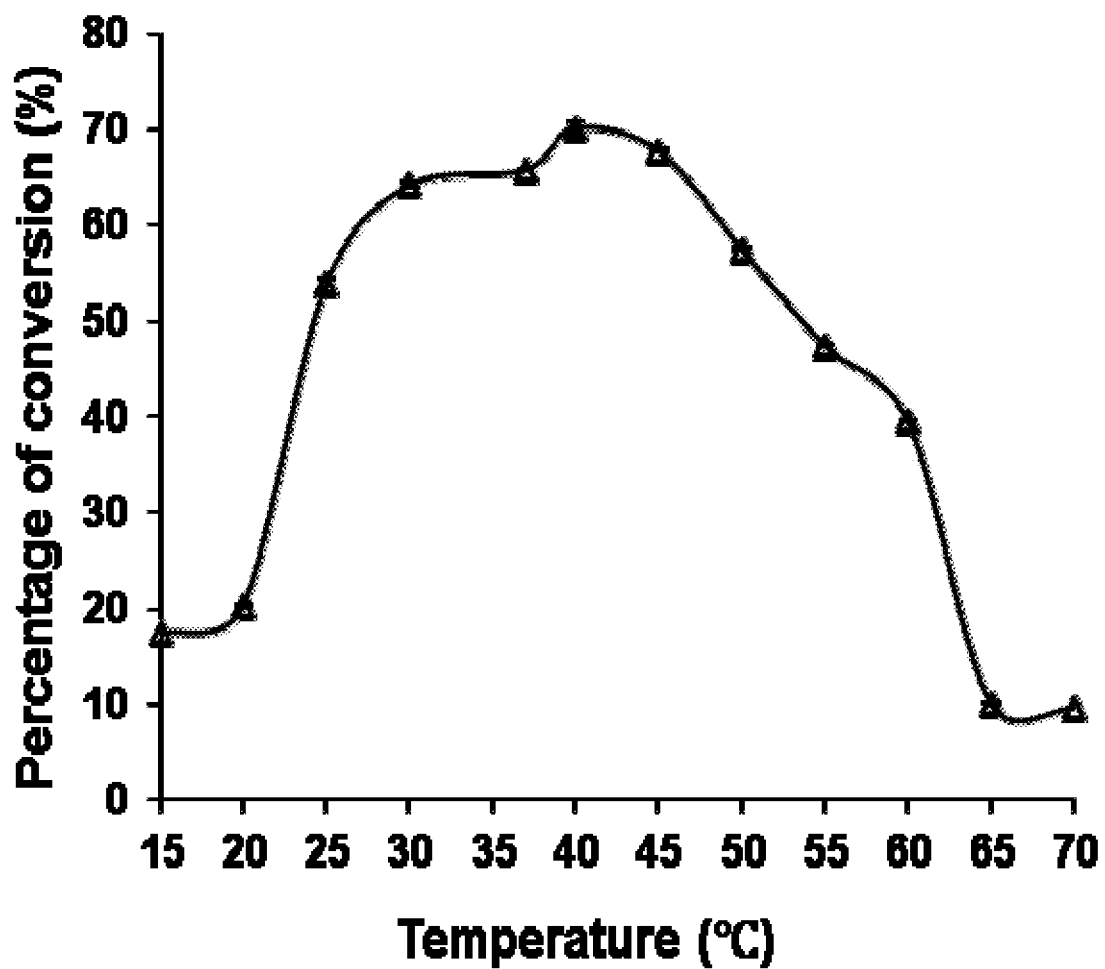
FIG. 6 shows the temperature profile of the α1-2-fucosyltransferase activity of His$_6$-Te2FT when Galβ1-3GlcNAcβ2AA was used as an acceptor substrate.

Since $His_6$-Te2FT was originated from a thermophilic cyanobacterium, its temperature profile was investigated. It was active in a broad temperature range of 25-60° C. with optimal activities observed in the range of 30-45° C. (FIG. 6). Low activity was observed at 15° C. and 20° C. and minimal activity was retained at 65° C. or 70° C.

Example 5

Effect of Freeze-Dry Cycle on His$_6$-Te2FT

Methods

Purified His$_6$-Te2FT samples were prepared essentially as described in Example 1, and were dialyzed against 20 mM Tris-HCl without glycerol and lyophilized. The Te2FT powders were stored at −70° C. for 20 days, or for several months. After that, the dried powder was dissolved in water and 20 mM Tris-HCl buffer, respectively. The activities of the lyophilized His$_6$-Te2FT samples were compared with the same amount and concentration of freshly prepared Te2FT samples. The reaction mixture was GDP-fucose (1 mM), Galβ1-3GlcNAcβ2AA, (1 mM), MgCl$_2$ (20 mM), and His$_6$-Te2FT (0.75 µg). All reactions were performed in duplicate and allowed to proceed for 10 minutes at 37° C.

Results

Figure 7:
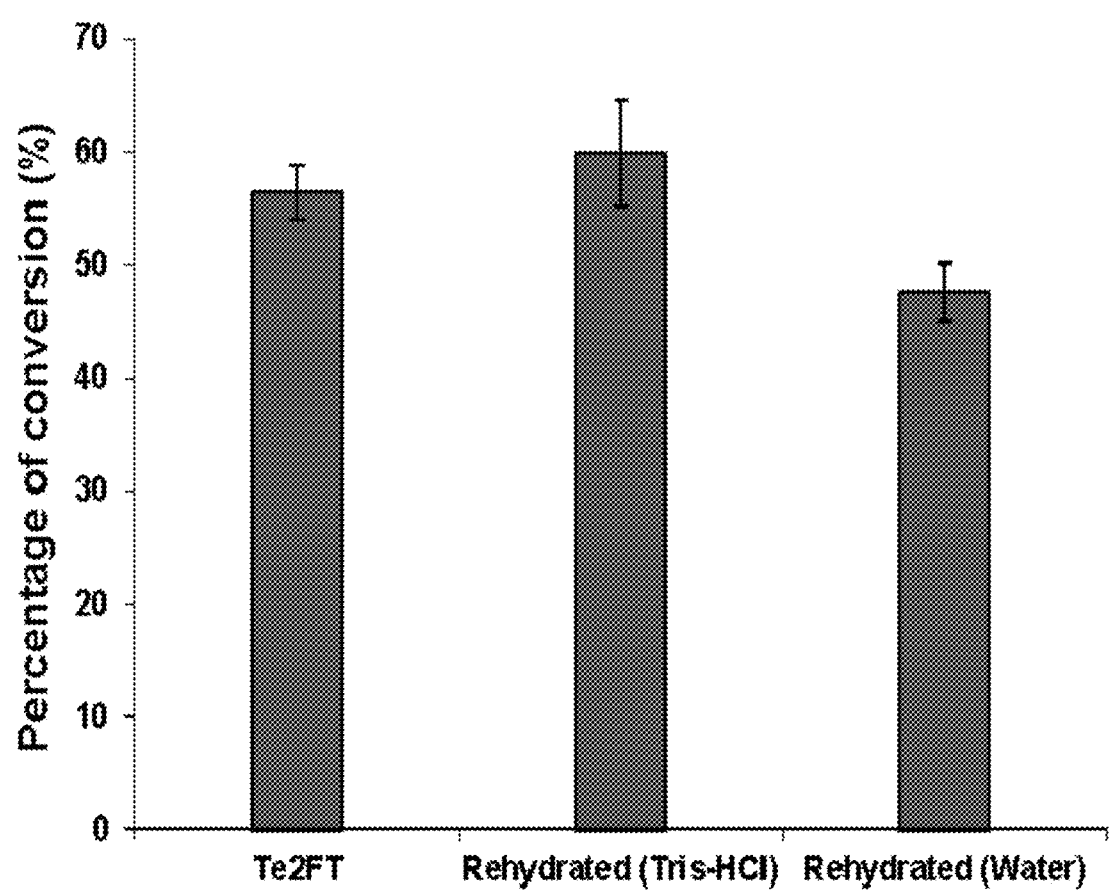
FIG. 7 shows the activities of His$_6$-Te2FT with or without lyophilization and rehydration when Galβ1-3GlcNAcβ2AA was used as an acceptor substrate.

The lyophilization experiment demonstrated His$_6$-Te2FT can survive a freeze-dry treatment (FIG. 7), even when the enzyme Te2FT is stored at −70° C. for several months. The enzyme maintains its fucosyltransferase activity similar to that obtained to freshly prepared preparations of TE2FT, indicating the potential for long term storage.

Example 6

Kinetic Studies

Kinetics of α1-2-Fucosyltransferase Activity By HPLC Assays

Typical enzymatic assays were carried out in duplicate in a total volume of 10 µL in Tris-HCl buffer (pH 6.0, 200 mM) containing MgCl$_2$ (20 mM), GDP-fucose, Galβ1-3GlcNAcβ2AA, and the recombinant His$_6$-Te2FT (0.75 µg). All reactions were allowed to proceed for 10 min at 37° C. Apparent kinetic parameters were obtained by varying the GDP-fucose concentration from 0.1 to 10.0 mM (0.1, 0.2, 0.4, 1.0, 5.0, and 10.0 mM) and a fixed concentration of Galβ1-3GlcNAcβ2AA (1 mM); or a fixed concentration of GDP-fucose (1 mM) and varied concentrations of Galβ1-3GlcNAcβ2AA from 0.1 to 10.0 mM (0.1, 0.2, 0.4, 5.0, and 10.0 mM). The reaction mixture was quenched by boiling for 2 minutes and diluted 60-fold for detection. Apparent kinetic parameters were obtained by fitting the data into the Michaelis-Menten equation using Grafit 5.0.

Results

Initial substrate specificity studies using various disaccharides as acceptor substrates indicated that His$_6$-Te2FT worked well with type I (Galβ1-3GlcNAcβOR) and its derivative (Gal1-3GlcNAcαOR), Type III (Galβ1-3GalNAcαOR), and type IV (Galβ1-3GalNAcβOR) acceptors for adding a fucose α1-2-linked to the terminal galactose (Gal) residue. However, type II (Galβ1-4GlcNAcβOR) and type V (Galβ1-4GlcβOR)[22] glycans were not good acceptors.

Kinetics studies of His$_6$-Te2FT using Galβ1-3GlcNAcβ2AA as an acceptor (Table 1) indicated its superior α1-2-fucosyltransferase activity. Compared to GST-WbsJ,[13] His$_6$Prop-WgbL,[15a] and Hp2FT, [10] His$_6$-Te2FT showed a significantly higher k$_{cat}$ value for GDP-fucose (201-, 6.7-, and 14.6-fold, respectively) and a higher affinity for the acceptor.

TABLE 1

| Activity | Substrate | k$_{cat}$ (min$^{-1}$) | K$_M$ (mM) | k$_{cat}$/K$_M$ (min$^{-1}$ mM$^{-1}$) |
|---|---|---|---|---|
| 2FT | Galβ1-3GlcNAcβ2AA | 20.0 ± 0.7 | 0.79 ± 0.11 | 25.3 |
|  | GDP-fucose | 26.3 ± 0.8 | 0.73 ± 0.68 | 36.1 |
| GDP-Fuc hydrolysis | GDP-fucose | 0.30 ± 0.06 | 0.56 ± 0.21 | 0.54 |

The catalytic efficiency of His$_6$-Te2FT was similar to that of Hp2FT but is superior to WbsJ and WbgL as reflected by a higher k$_{cat}$/KM value for GDP-Fuc (29.2-fold and 2.5-fold higher).

Kinetics of GDP-Fucose Hydrolysis By Capillary Electrophoresis Assays

The enzymatic assays were carried out in duplicate in a total volume of 10 µL in Tris-HCl buffer (200 mM, pH 9.0) containing MgCl$_2$ (20 mM), GDP-fucose and the recombinant protein (4.5 µg). Reactions were allowed to proceed for 30 min at 37° C. Apparent kinetic parameters were obtained by varying the final GDP-fucose concentration from 0.4 to 2.0 mM (0.4, 0.5, 0.6, 0.8, 1.0 and 2.0 mM). Apparent kinetic parameters were obtained by fitting the data (the average values of duplicate assay results) into the Michaelis-Menten equation using Grafit 5.0.

Results

The GDP-fucose (donor) hydrolysis activity (kcat/KM=0.54 min-1 mM-1) of His6-Te2FT (Table 1) was 47-fold weaker than its α1-2-fucosyltransferase activity and much lower than the donor hydrolysis activity of Hp2FT (6.07 min-1 mM-1).7 These data indicate that His6-Te2FT is a superior catalyst for enzymatic synthesis of α1-2-linked fucosides.

Example 7

Acceptor Substrate Specificity Studies of His$_6$-Te2FT

General Synthetic Methods

Chemicals were purchased and used without further purification. $^1$H NMR (800 MHz) and $^{13}$C NMR (200 MHz) spectra were recorded on a Bruker Avance-800 NMR spectrometer. High resolution electrospray ionization (ESI) mass spectra were obtained using Thermo Electron LTQ-Orbitrap Hybrid MS at the Mass Spectrometry Facility in the University of California, Davis. Silica gel 60 Å (230-400 mesh, Sorbent Technologies) was used for flash column chromatography. Thin-layer chromatography (TLC, Sorbent Technologies) was performed on silica gel plates using anisaldehyde sugar stain or 5% sulfuric acid in ethanol stain for detection. Gel filtration chromatography was performed with a column (100 cm×2.5 cm) packed with Bio-Gel P-2 Fine resins (Bio-Rad, Hercules, Calif., USA). D-Lactose, D-galactose, and N-acetyl-D-glucosamine (D-GlcNAc) were from Fisher Scientific (Pittsburgh, Pa., USA). L-Fucose was from V-LABS (Covington, La., USA). Lacto-N-tetraose (LNT) was from Elicityl (Crolles, France). Guanidine 5'-triphosphate (GTP) was from Hangzhou Meiya Pharmacy (Hangzhou, China). Adenosine 5'-triphosphate (ATP) was from Beta Pharma Scientific, Inc. (Branford, Connectic, USA). Recombinant enzymes *Bacteroides fragilis* strain NCTC9343 bifunctional L-fucokinase/GDP-fucose pyrophosphorylase (FKP)[24] and *Pasteurella multocida* inorganic pyrophosphatase (PmPpA)[25] were expressed and purified as described previously. Compounds Galβ1-3GalNAcαProN₃, Galβ1-3GalNAcβProN₃, Galβ1-3GlcNAcαProN₃, Galβ1-3GlcNAcβProN₃ were synthesized as described previously.[34]

Synthesis of 2AA-Labeled Saccharides:
Galβ1-3GlcNAcβ2AA, Galβ1-4GlcNAcβ2AA, and Galβ1-4Glcβ2AA Galβ1-3GlcNAcβProN₃, Galβ1-4GlcNAcβProN₃, or Galβ1-4GlcβProN₃ (50-60 mg) was dissolved in 5 mL water and 100 mg Pd/C was added. The mixture was shaken under H2 (4 Bar) for 1 h and filtered. The filtrate was evaporated to dryness to afford the corresponding amine product which was used in the next step without purification. To the solution of glycan-amine in 5 mL anhydrous DMF, was added triethylamine (60 µL) under argon. Two equivalents of N-hydroxysuccinimidyl 2AA were then added at 0° C. The resulting solution was stirred at room temperature overnight. The reaction mixture was concentrated and the residue was purified by flash column chromatography (EA:MeOH:H₂O=8:2:1, by volume) to produce the corresponding 2AA-labeled oligosaccharides.

Results

Synthesis of Galβ1-3GlcNAcβ2AA

Galβ1-3GlcNAcβ2AA. 51 mg, 92%. ¹H NMR (800 MHz, D₂O): δ 7.91 (d, J=8.0 Hz, 1H), 7.84 (d, J=8.0 Hz, 1H), 7.59 (t, J=8.0 Hz, 1H), 7.26 (t, J=8.0 Hz, 1H), 4.43 (d, J=8.8 Hz, 1H), 4.37 (d, J=8.0 Hz, 1H), 3.88 (d, J=4.0 Hz, 1H), 3.87 (s, 3H), 3.86-3.84 (m, 2H), 3.79-3.59 (m, 6H), 3.61 (dd, J=9.6 and 3.2 Hz, 1H), 3.53 (m, 1H), 3.49 (t, J=8.0 Hz, 1H), 3.48 (t, J=8.8 Hz, 1H), 3.37 (m, 1H), 3.24 (m, 1H), 3.14 (m, 1H), 2.71 (t, J=7.2 Hz, 2H), 2.58 (t, J=7.2 Hz, 2H), 1.98 (s, 3H), 1.71 (m, 2H); ¹³C NMR (200 MHz, D₂O): δ 174.48, 174.24, 173.09, 168.90, 137.18, 133.93, 130.77, 124.95, 122.86, 120.11, 103.40, 100.77, 82.39, 75.19, 75.15, 72.35, 70.53, 68.55, 68.38, 67.48, 60.87, 60.56, 54.38, 52.64, 35.98, 32.29, 30.75, 28.20, 22.07. HRMS (ESI) m/z calcd for $C_{29}H_{43}N_3NaO_{15}$ (M+Na) 696.2592, found 696.2585.

Synthesis of Galβ1-4GlcNAcβ2AA

Galβ1-4GlcNAcβ2AA. 68 mg, 90%. ¹H NMR (800 MHz, D₂O): δ 7.96 (d, J=8.0 Hz, 1H), 7.81 (d, J=8.0 Hz, 1H), 7.62 (t, J=8.0 Hz, 1H), 7.31 (t, J=8.0 Hz, 1H), 4.42 (d, J=8.0 Hz, 1H), 4.40 (d, J=8.8 Hz, 1H), 3.98-3.51 (m, 16H), 3.46 (m, 1H), 3.25 (m, 1H), 3.14 (m, 1H), 2.74 (t, J=8.0 Hz, 2H), 2.59 (t, J=8.0 Hz, 2H), 1.98 (s, 3H), 1.71 (m, 2H); ¹³C NMR (200 MHz, D₂O): δ 174.37, 174.31, 173.31, 168.97, 136.87, 133.85, 130.76, 125.20, 123.32, 120.87, 102.75, 100.97, 78.30, 75.21, 74.57, 72.40, 72.30, 70.82, 68.41, 67.47, 60.88, 59.89, 54.90, 52.65, 35.95, 32.17, 30.76, 28.18, 21.99. HRMS (ESI) m/z calcd for $C_{29}H_{43}N_3NaO_{15}$ (M+Na) 696.2592, found 696.2589.

Synthesis of Galβ1-4Glcβ2AA

Galβ1-4Glcβ2AA. 55 mg, 91%. ¹H NMR (800 MHz, D₂O): δ 7.95 (d, J=8.0 Hz, 1H), 7.84 (d, J=8.8 Hz, 1H), 7.61 (t, J=8.0 Hz, 1H), 7.30 (t, J=8.0 Hz, 1H), 4.41 (d, J=8.0 Hz, 1H), 4.33 (d, J=8.0 Hz, 1H), 3.92-3.52 (m, 13H), 3.45 (m, 1H), 3.31-3.23 (m, 5H), 2.74 (t, J=7.2 Hz, 2H), 2.59 (t, J=7.2 Hz, 2H), 1.77 (m, 2H); ¹³C NMR (200 MHz, D₂O): δ 174.34, 173.23, 168.95, 137.03, 133.90, 130.78, 125.10, 123.12, 120.52, 102.81, 101.93, 78.24, 75.22, 74.58, 74.21, 72.65, 72.41, 70.82, 68.41, 67.50, 60.89, 59.91, 52.65, 36.04, 32.27, 30.85, 28.24. HRMS (ESI) m/z calcd for $C_{27}H_{40}N_2NaO_{15}$ (M+Na) 655.2326, found 655.2326.

Example 8

One-Pot Three-Enzyme Preparative-Scale Synthesis of α1-2-Linked Fucosides

Methods

Figure 8:
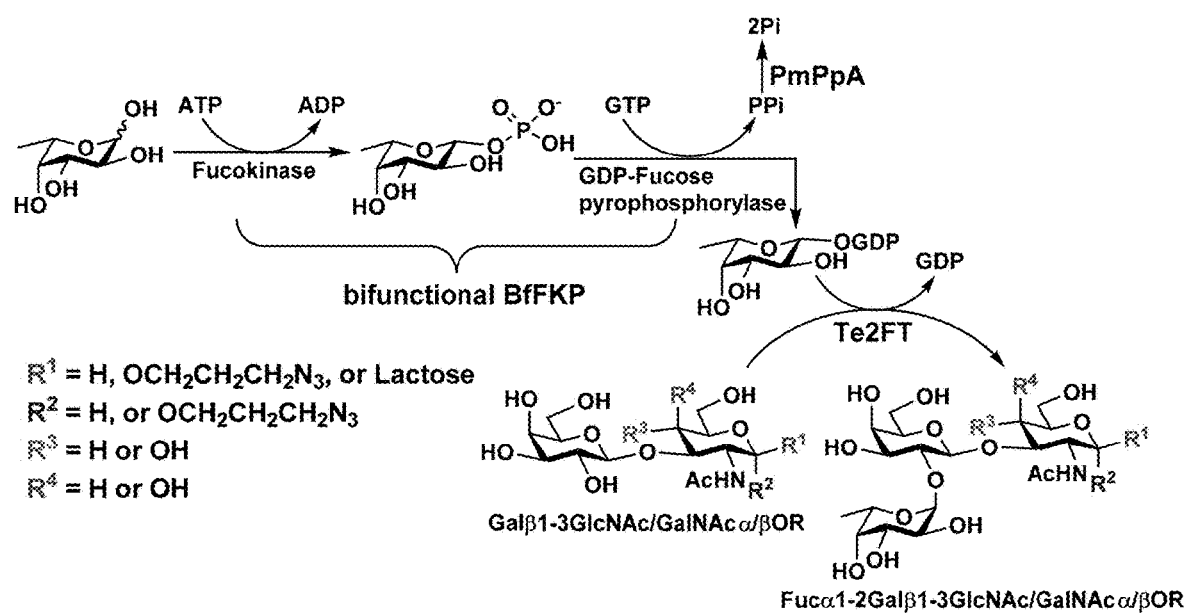
FIG. 8 shows a schematic diagram for the one-pot, three-enzyme synthesis of human blood group H antigens from a recombinant BfFKP, PmPpA, and Te2FT.

Galactoside (30-60 mg each, 1 equiv.), L-fucose (1.3 equiv.), ATP (1.3 equiv.), and GTP (1.3 equiv.) were dissolved in Tris-HCl buffer (8 mL, 100 mM, pH 7.5) containing MgCl₂ (20 mM) and recombinant bifunctional L-fucokinase/GDP-fucose pyrophosphorylase (FKP, 1.5 mg),[24] Pasteurella multocida inorganic pyrophosphatase (PmPpA) (1.0 mg), and His₆-Te2FT (1.5-2.0 mg) (FIG. 8). All other reactions were carried out at pH 7.5. All reactions were incubated in an incubator shaker at 37° C. for around 1-2 days with agitation at 100 rpm. The product formation was monitored by mass spectrometry. When an optimal yield was achieved, the reaction was stopped by adding the same volume of cold ethanol (EtOH) and kept at 4° C. for 30 min. The mixture was centrifuged at 7000 rpm for 30 minutes and the precipitates were removed. The supernatant was concentrated, passed through a BioGel P-2 gel filtration column, and eluted with water to obtain partially purified product. A silica gel column was then used for further purification using EtOAc:MeOH:H₂O=5:2:1 (by volume) as the mobile phase. The final pure fucosylated products was obtained by passing through a BioGel P-2 gel filtration column again for removing any silica gel dissolved.

Results

The synthetic application of Te2FT was explored in an efficient one-pot three-enzyme (OP3E) fucosylation system (FIG. 8) for synthesizing various α1-2-linked fucosides. In this system, recombinant bifunctional L-fucokinase/GDP-fucose pyrophosphorylase from *Bacteroides fragilis* strain NCTC9343 (BfFKP)[24] was used for catalyzing the formation of GDP-fucose from fucose, adenosine 5'-triphosphate (ATP), and guanidine 5'-triphosphate (GTP) to provide the donor substrate for Te2FT. *Pasteurella multocida* inorganic pyrophosphatase (PmPpA)[25] was used to break down the pyrophosphate by-product to shift the reaction towards the formation of GDP-fucose. As shown in Table 2, the OP3E fucosylation of β1-3-linked galactosides was successfully accomplished with 96%, 95%, 95%, and 98% yields, respectively, to produce desired human blood group H antigens, Fucα1-2Galβ1-3GlcNAcβProN₃ (1, a type I H antigen), Fucα1-2Galβ1-3GlcNAcαProN₃ (2, a type I H antigen derivative), Fucα1-2Galβ1-3GalNAcαProN₃ (3, a type III H antigen), and Fucα1-2Galβ1-3GalNAcβProN₃ (4, a type IV H antigen).

TABLE 2

| Acceptor | Product | Yield (%) | Amount (mg) |
| --- | --- | --- | --- |
| Galβ1-3GlcNAcβProN₃ | Fucα1-2Galβ1-3GlcNAcβProN₃ (1) | 96 | 50.5 |
| Galβ1-3GlcNAcαProN₃ | Fucα1-2Galβ1-3GlcNAcαProN₃ (2) | 95 | 51.3 |

TABLE 2-continued

| Acceptor | Product | Yield (%) | Amount (mg) |
|---|---|---|---|
| Galβ1-3GalNAcαProN₃ | Fucα1-2Galβ1-3GalNAcαProN₃ (3) | 95 | 35.7 |
| Galβ1-3GalNAcβProN₃ | Fucα1-2Galβ1-3GalNAcβProN₃ (4) | 98 | 43.8 |
| LNT | Fucα1-2LNT or LNFP 1 (5) | 94 | 68.1 |
|  |  | 95 | 1146 |

Results

Fucα1-2Galβ1-3GalNAcαProN₃ (1) 35.7 mg 95%, $^1$H NMR (800 MHz, D$_2$O): δ 5.17 (d, J=4.0 Hz, 1H), 4.62 (d, J=8.0 Hz, 1H), 4.21 (dd, J=13.6 and 6.4 Hz, 1H), 4.12 (t, J=9.6 Hz, 1H), 3.84-3.42 (m, 19H), 2.04 (s, 3H), 1.87 (m, 2H), 1.19 (d, J=7.2 Hz, 3H); $^{13}$C NMR (200 MHz, D$_2$O): δ 173.52, 101.91, 99.14, 96.63, 76.09, 74.89, 73.90, 73.39, 71.71, 70.43, 69.46, 68.95, 67.94, 66.68, 64.64, 62.55, 61.08, 60.82, 49.41, 48.01, 27.91, 21.78, 15.26. HRMS (ESI) m/z calculated for C$_{23}$H$_{40}$N$_4$NaO$_{15}$ (M+Na) 635.2388, found 635.2383.

Fucα1-2Gal1-3GalNAcβProN₃ (2). 43.8 mg, 98%, $^1$H NMR (800 MHz, D$_2$O): δ 5.21 (d, J=4.8 Hz, 1H), 4.59 (d, J=8.0 Hz, 1H), 4.31 (d, J=8.0 Hz, 1H), 4.21 (dd, J=13.6 and 7.2 Hz, 1H), 4.08 (d, J=2.4 Hz, 1H), 3.97-3.58 (m, 16H), 3.34 (m, 2H), 2.04 (s, 3H), 1.81 (m, 2H), 1.19 (d, J=6.4 Hz, 3H); $^{13}$C NMR (200 MHz, D$_2$O): δ 173.58, 102.54, 101.95, 99.08, 76.48, 75.88, 74.94, 74.67, 73.43, 71.66, 69.39, 68.99, 68.38, 67.90, 66.86, 66.68, 60.86, 60.82, 51.29, 47.61, 28.07, 22.14, 15.14. HRMS (ESI) m/z calculated for C$_{23}$H$_{40}$N$_4$NaO$_{15}$ (M+Na) 635.2388, found 635.2395.

Fucα1-2Galβ1-3GlcNAcαProN₃ (3). 51.3 mg, 95%, $^1$H NMR (800 MHz, D$_2$O): δ 5.21 (d, J=3.2 Hz, 1H), 4.85 (d, J=3.2 Hz, 1H), 4.62 (d, J=8.0 Hz, 1H), 4.21 (dd, J=13.6 and 6.4 Hz, 1H), 4.17-3.41 (m, 19H), 2.03 (s, 3H), 1.87 (m, 2H), 1.18 (d, J=6.4 Hz, 3H); $^{13}$C NMR (200 MHz, D$_2$O): δ 173.54, 100.12, 99.36, 96.82, 76.48, 75.27, 74.89, 73.38, 71.71, 71.48, 69.38, 69.03, 68.54, 67.91, 66.37, 64.77, 60.96, 60.31, 53.25, 48.03, 27.91, 21.72, 15.19. HRMS (ESI) m/z calculated for C$_{23}$H$_{40}$N$_4$NaO$_{15}$ (M+Na) 635.2388, found 635.2391.

Fucα1-2Galβ1-3GlcNAcβProN₃ (4). 50.5 mg, 96%, $^1$H NMR (800 MHz, D$_2$O): δ 5.16 (d, J=3.2 Hz, 1H), 4.62 (d, J=7.2 Hz, 1H), 4.40 (d, J=7.2 Hz, 1H), 4.27-3.32 (m, 20H), 2.05 (s, 3H), 1.81 (m, 2H), 1.20 (d, J=6.4 Hz, 3H); $^{13}$C NMR (200 MHz, D$_2$O): • 173.55, 101.66, 100.07, 99.37, 77.11, 76.51, 75.29, 74.93, 73.32, 71.66, 69.29, 69.00, 68.61, 67.91, 66.97, 66.37, 61.03, 60.55, 54.73, 47.61, 28.04, 22.06, 15.07. HRMS (ESI) m/z calculated for C$_{23}$H$_{40}$N$_4$NaO$_{15}$ (M+Na) 635.2388, found 635.2393.

Methods

Figure 9:
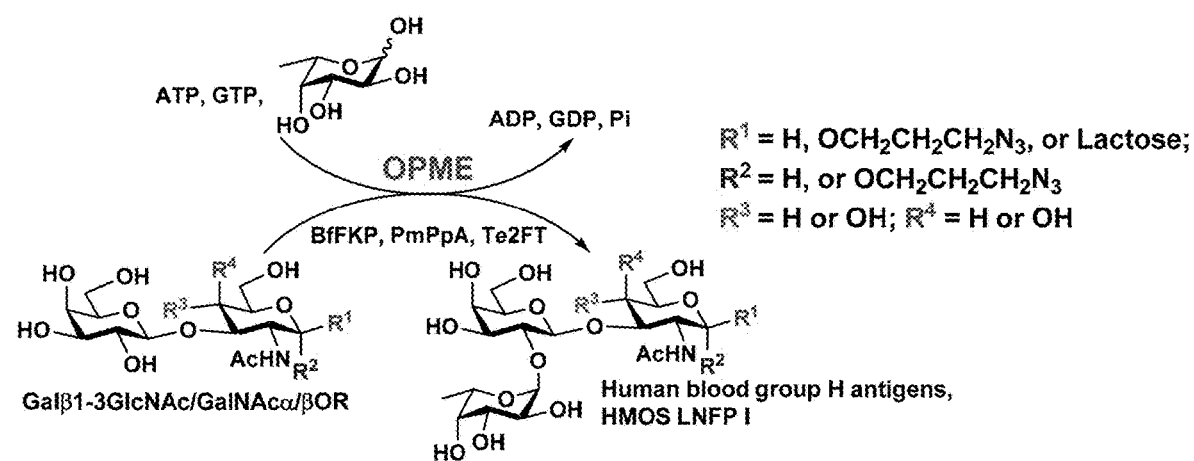
FIG. 9 shows a schematic diagram for the one-pot, three-enzyme synthesis of lacto-N-fucopentaose (LNFP I) from a recombinant BfFKP, PmPpA, and Te2FT.
Figure 10:
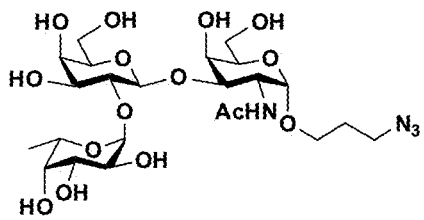
FIG. 10 shows schematic diagrams for various Te2FT-catalyzed products from the fucosylation systems of FIGS. 8 and 9.
Figure 10:
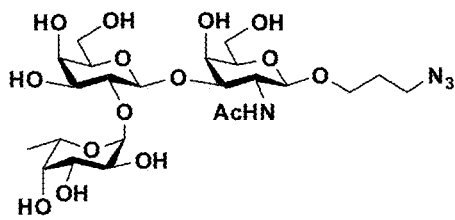
Figure 10:
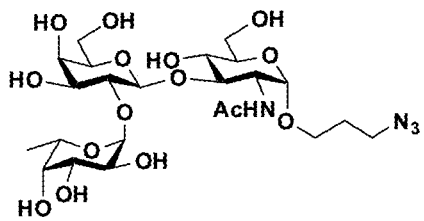
Figure 10:
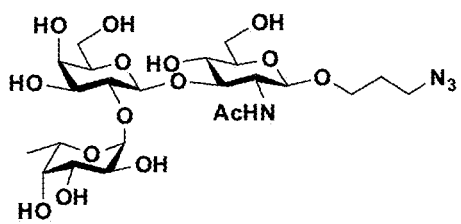
Figure 10:
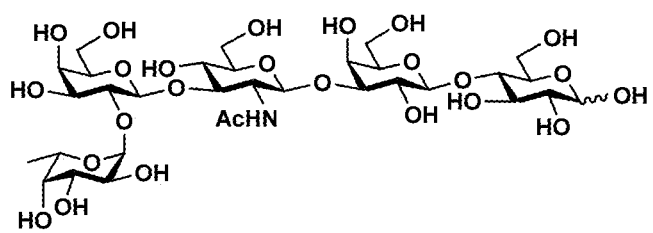

The synthetic application of Te2FT was explored in another efficient one-pot three-enzyme (OP3E) fucosylation system (FIG. 9) for synthesizing a human milk oligosaccharide (HMOS). In this system, recombinant bifunctional L-fucokinase/GDP-fucose pyrophosphorylase from Bacteroides fragilis strain NCTC9343 (BfFKP)[24] was used for catalyzing the formation of GDP-fucose from fucose, adenosine 5'-triphosphate (ATP), and guanidine 5'-triphosphate (GTP) to provide the donor substrate for Te2FT. Pasteurella multocida inorganic pyrophosphatase (PmPpA)[25] was used to break down the pyrophosphate by-product to shift the reaction towards the formation of GDP-fucose. As shown in Table 2, the OP3E fucosylation of β1-3-linked galactosides was successfully accomplished with a 94% yield to produce the desired HMOS. NMR and HRMS analyses were carried out to confirm the identify and the purity of the product.

Results

Human milk tetrasaccharide lacto-N-tetraose (LNT) (Galβ1-3GlcNAcβ1-3Galβ1-4Glc) was also an excellent acceptor for His$_6$-Te2FT and the OP3E synthesis of Fucα1-2LNT (5), a human milk pentasaccharide also known as lacto-N-fucopentaose I (LNFP I), was achieved in a preparative scale (68.1 mg) with an excellent 94% yield.

Fucα1-2LNT or LNFP I (5). 68.1 mg, 94% and 1.146 g, 95%, $^1$H NMR (800 MHz, D$_2$O): δ 5.19 (d, J=4.0 Hz, 0.4H), 5.17 (d, J=4.0 Hz, 1H), 4.64 (d, J=8.0 Hz, 0.6H), 4.62 (d, J=8.0 Hz, 1H), 4.60 (dd, J=8.0 and 2.4 Hz, 1H), 4.40 (d, J=8.0 Hz, 1H), 4.26 (dd, J=13.6 and 6.4 Hz, 1H), 4.15 (d, J=3.2 Hz, 1H), 3.98-3.24 (m, 26H), 2.03 (s, 3H), 1.21 (d, J=6.4 Hz, 3H); $^{13}$C NMR (200 MHz, D$_2$O): δ 174.13, 103.11, 102.82, 102.78, 100.12, 99.39, 95.60, 91.68, 81.43, 81.40, 78.06, 77.98, 77.00, 76.54, 75.11, 74.93, 74.69, 74.19, 73.65, 73.35, 71.72, 71.24, 70.99, 70.10, 70.07, 70.02, 69.29, 68.99, 68.49, 68.47, 68.33, 67.91, 66.36, 61.02, 60.83, 60.25, 59.92, 59.79, 54.84, 22.00, 15.13. HRMS (ESI) m/z calculated for C$_{32}$H$_{55}$NnaO$_{25}$ (M+Na) 876.2961, found 876.2959.

Example 9

Gram-Scale Synthesis of Fucα1-2LNT (LNFP I) (Fucα1-2Galβ1-3GlcNAcβ1-3Galβ1-4Glc)

Methods

Lacto-N-tetraose (LNT, 1 g), L-fucose (1.5 equiv.), ATP (1.5 equiv.), and GTP (1.5 equiv.) were dissolved in Tris-HCl buffer (140 mL, 100 mM, pH 7.0) containing MgCl$_2$ (20 mM) and appropriate amounts of a recombinant L-fucokinase/GDP-fucose pyrophosphorylase (FKP, 30 mg), Pasteurella multocida inorganic pyrophosphatase (PmPpA, 30 mg), and His$_6$-Te2FT (25-30 mg). The reactions were incubated in an incubator shaker at 37° C. for 1-2 days with agitation at 100 rpm. The product formation was monitored by mass spectrometry and thin layer chromatography (TLC). When an optimal yield was achieved, the reaction was stopped by adding the same volume of cold ethanol (EtOH) and kept at 4° C. for 30 min. The mixture was then centrifuged at 7000 rpm for 30 minutes and the precipitates were removed. The supernatant was concentrated, passed through a BioGel P-2 gel filtration column, and eluted with water to obtain partially purified product.

A silica gel column was used for further purification of LNFP-I using EtOAc:MeOH:H$_2$O=5:3:2 (by volume) as the mobile phase. The obtained LNFP I sample was further purified used activated charcoal. To a 50 mL centrifuge tube, 2 g of charcoal were added. Ethanol (absolute ethanol or 90%+ethanol) (30 mL) was added to the tube and it was mixed thoroughly by inverting the tube. The tube was centrifuged at 12,000 rpm for 30 min and the supernatant was decanted. The process was repeated once. Water (30 mL) was added to tube and it was mixed thoroughly by inverting the tube followed by centrifugation for 30 min and supernatant was decanted. The tube was left at room temperature for 30 min in a fume hood to evaporate any residual of ethanol. Crude LNFP I (100 mg) was added to tube with 30 mL of water and the tube was mixed thoroughly. The tube was then put into a shaker with agitation (100 rpm) for 1-2 h at 37° C. The tube was centrifuged at 12,000 rpm for 30 min to spin down the charcoal and the supernatant was discarded by decanting. Finally, 50% methanol (30 mL) was added to tube and it was mixed thoroughly by inverting the tube followed by centrifugation at 12,000 rpm for 30 min. The supernatant was collected and passed through a paper filter to remove any charcoal particles. The process was repeated. The filtered solution was combined and lyophilized to produce pure LNFP I as a white solid with an excellent yield of 95%. NMR and HRMS analyses were carried out to confirm the identify and the purity of the product.

Results

Pure LNFP I in an amount of 1.146 gram was successfully obtained with an excellent 95% yield. It should be noted that the purification of the product in the gram-scale synthesis of LNFP I was greatly simplified by using activated charcoal which was very efficient in removing nucleotides in the reaction mixtures. Due to the complete consumption of the acceptor LNT in the reaction mixture, separating the pentasaccharide product from other components with smaller molecular weights was conveniently done by a gel filtration column which served similarly as desalting. In a second attempt using the one-pot three enzyme synthesis system, the amount of pure LNFP I obtained was 8 grams, thereby demonstrating the large scale synthesis of LNFP I via the OPME system disclosed herein.

Example 10

Growth of B. infantis 15697 and B. animalis 27536 on Medium Supplemented with Glucose (Glc), Human Milk Oligosaccharides (HMOS), and LNFP I Methods B. infantis 15697 and B. animalis 27536 were tested for growth in the presence of glucose, HMOS, and LNFP I. Growth assays were performed as previously described.[35] Briefly, two microliters of each resulting overnight culture was used to inoculate 150 μL of modified MRS medium (mMRS), devoid of glucose and supplemented with 2% (wt/vol) of each sterile-filtered substrate as the sole carbohydrate source. The medium was supplemented with 0.05% (wt/vol) 1-cysteine, and in all the cases the cultures in the wells of the microtiter plates were covered with 30 μL of sterile mineral oil to avoid evaporation. The incubations were carried out at 37° C. in an anaerobic chamber (Coy Laboratory Products). Cell growth was monitored in real time by assessing optical density at 600 nm (OD600) using a BioTek PowerWave 340 plate reader (BioTek, Winoosky, Vt.) every 30 min, preceded by 30 seconds of shaking at variable speed. Two biological replicates and three technical replicates each were performed for every strain. Fermentations were carried out in triplicate.

Results

LNFP I was identified in 1956 as one of the HMOS structures.[26] It is missing in the milk of Le$^{a+b-}$ non-secretors,[9] otherwisely it is an abundant HMOS species (1.2-1.7 g/liter) in pooled human milk.[3c1] It is not presented in the milk or the colostrum of cows,[27] pigs,[28] or other domestic animals.[27] Therefore it is not readily accessible from natural sources by purification. Chemical synthesis of LNFP I with a β-linked pentanylamino aglycon from a protected tetrasaccharide precursor obtained by a one-pot chemical synthetic procedure was achieved in four steps with 49% yield.[29] LNFP I was also synthesized from LNT and GDP-fucose using a recombinant human FUT1 expressed in a baculovirus system (3.0 mg, 71% yield)[30] and in whole-cell recombinant E. coli expressing HpFutC (59.4 mg). The facile synthesis of lacto-N-fucopentaose I (LNFP I) is therefore of significant commercial importance. The OP3E system presented here is a more efficient and an economically feasible approach for large-scale production of LNFP I and allows downstream investigation of its potential prebiotic application.

Figure 11A:
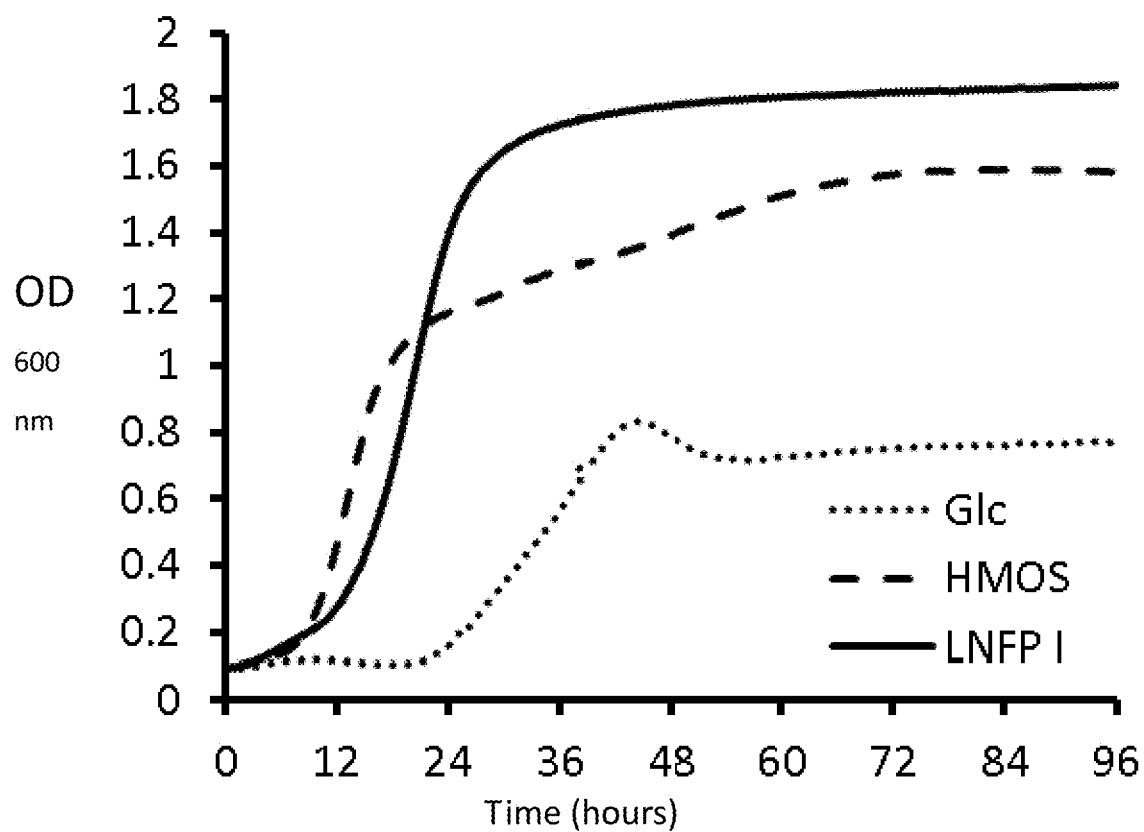
FIGS. 11A and 11B show growth of bifidobacterial strains *B. infantis* (FIG. 11A) and *B. lactis* (FIG. 11B) on mMRS medium supplemented with 2% (wt/vol) glucose (dotted line), HMOS (dashed line), or LNFP I (solid line).
Figure 11B:
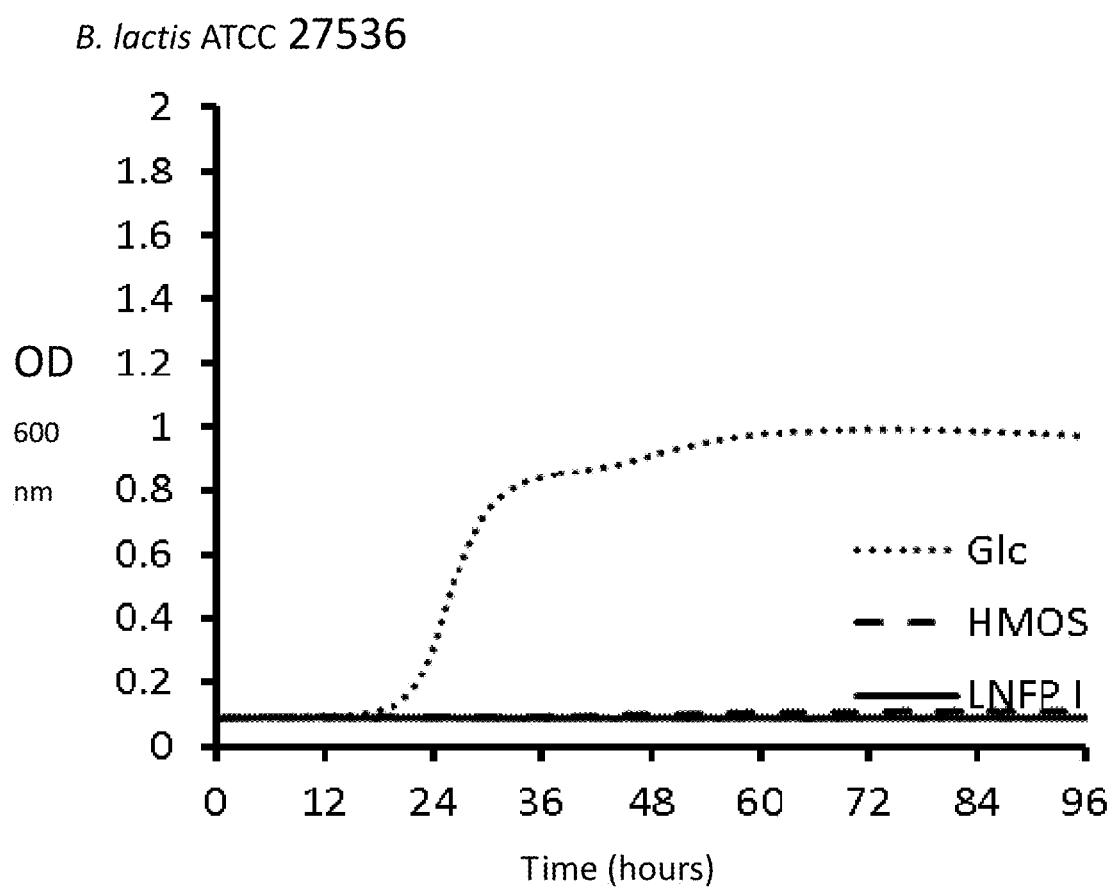

The ability of LNFP I in serving as the sole carbon source for the growth of bifidobacteria was examined. Media containing HMOS (a mixture of oligosaccharides isolated from human milk)[31] or glucose were used as controls. Bifidobacterium longum subsp. infantis (B. infantis) ATCC 15697 grew well on LNFP I and HMOS with a similar pattern which was remarkably faster than its growth on glucose (FIG. 11). To establish specificity, LNFP I was tested for its ability to support the growth of Bifidobacterium animalis subsp. lactis (B. lactis) ATCC 27536, a subspecies that did not grow on HMOS.[32] B. lactis failed to grow on either LNFP I or HMOS, while it showed a similar growth pattern to B. infantis in the presence of glucose (FIG. 11B). Selective growth of B. infantis on a specific fucosylated HMOS species like LNFP I provides a molecular rationale for the unique enrichment of B. infantis and other infant-borne bifidobacteria in the nursing infant gastrointestinal tract by breastfeeding.[33]

In conclusion, Te2FT with a good recombinant expression level and high activity is an important tool for large-scale enzymatic synthesis of various biologically important α1-2-fucosides. We demonstrated that a one-pot multienzyme (OPME) fucosylation system is a highly effective system for chemoenzymatic and enzymatic synthesis of fucosides. The gram-scale synthesis of fucosylated human milk oligosaccharide LNFP I allowed the performance of bacteria growth study which showed that LNFP I was selectively consumed as a carbon source by B. infantis but not B. lactis. Therefore, LNFP I is a potential prebiotic candidate for further development.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

REFERENCES

[1] D. J. Becker, J. B. Lowe, Glycobiology 2003, 13, 41R-53R.
[2] a) Z. Tu, Y. N. Lin, C. H. Lin, Chem. Soc. Rev. 2013, 42, 4459-4475; b) J. Peter-Katalinic, Methods Enzymol. 2005, 405, 139-171.
[3] a) D. S. Newburg, G. M. Ruiz-Palacios, A. L. Morrow, Annu. Rev. Nutr. 2005, 25, 37-58; b) X. Chen in Advances in Carbohydrate Chemistry and Biochemistry, Vol. 72, (Eds.: D. C. Baker, D. Horton), Academic Press, ACCB, UK, 2015, pp. 113-190; c) C. Kunz, S. Rudloff, W. Baier, N. Klein, S. Strobel, Annu. Rev. Nutr. 2000, 20, 699-722; d) J. T. Smilowitz, C. B. Lebrilla, D. A. Mills, J. B. German, S. L. Freeman, Annu. Rev. Nutr. 2014, 34, 143-169.

[4] G. M. Ruiz-Palacios, L. E. Cervantes, P. Ramos, B. Chavez-Munguia, D. S. Newburg, J. Biol. Chem. 2003, 278, 14112-14120.

[5] P. Chaturvedi, C. D. Warren, M. Altaye, A. L. Morrow, G. Ruiz-Palacios, L. K. Pickering, D. S. Newburg, Glycobiology 2001, 11, 365-372.

[6] R. D. Larsen, L. K. Ernst, R. P. Nair, J. B. Lowe, Proc. Natl. Acad. Sci. U.S.A 1990, 87, 6674-6678.

[7] a) S. Rouquier, J. B. Lowe, R. J. Kelly, A. L. Fertitta, G. G. Lennon, D. Giorgi, J. Biol. Chem. 1995, 270, 4632-4639; b) R. J. Kelly, S. Rouquier, D. Giorgi, G. G. Lennon, J. B. Lowe, J. Biol. Chem. 1995, 270, 4640-4649.

[8] a) L. Shen, E. F. Grollman, V. Ginsburg, Proc. Natl. Acad. Sci. U.S.A 1968, 59, 224-230; b) E. F. Grollman, V. Ginsburg, Biochem. Biophys. Res. Commun. 1967, 28, 50-53.

[9] A. Kobata, V. Ginsburg, M. Tsuda, Arch. Biochem. Biophys. 1969, 130, 509-513.

[10] a) G. Wang, D. A. Rasko, R. Sherburne, D. E. Taylor, Mol. Microbiol. 1999, 31, 1265-1274; b) D. B. Stein, Y.-N. Lin, C.-H. Lin, Adv. Synth. Catal. 2008, 350, 2313-2321.

[11] H. Guo, W. Yi, J. Shao, Y. Lu, W. Zhang, J. Song, P. G. Wang, Appl. Environ. Microbiol. 2005, 71, 7995-8001.

[12] W. Yi, J. Shao, L. Zhu, M. Li, M. Singh, Y. Lu, S. Lin, H. Li, K. Ryu, J. Shen, H. Guo, Q. Yao, C. A. Bush, P. G. Wang, J. Am. Chem. Soc. 2005, 127, 2040-2041.

[13] a) J. Shao, M. Li, Q. Jia, Y. Lu, P. G. Wang, FEBS Lett. 2003, 553, 99-103; b) M. Li, J. Shen, X. Liu, J. Shao, W. Yi, C. S. Chow, P. G. Wang, Biochemistry 2008, 47, 11590-11597; c) M. Li, X. W. Liu, J. Shao, J. Shen, Q. Jia, W. Yi, J. K. Song, R. Woodward, C. S. Chow, P. G. Wang, Biochemistry 2008, 47, 378-387.

[14] N. Pettit, T. Styslinger, Z. Mei, W. Han, G. Zhao, P. G. Wang, Biochem. Biophys. Res. Commun. 2010, 402, 190-195.

[15] a) L. Engels, L. Elling, Glycobiology 2014, 24, 170-178; b) Y. Liu, C. DebRoy, P. Fratamico, Mol. Cell. Probes 2007, 21, 295-302.

[16] Y. Nakamura, T. Kaneko, S. Sato, M. Ikeuchi, H. Katoh, S. Sasamoto, A. Watanabe, M. Iriguchi, K. Kawashima, T. Kimura, Y. Kishida, C. Kiyokawa, M. Kohara, M. Matsumoto, A. Matsuno, N. Nakazaki, S. Shimpo, M. Sugimoto, C. Takeuchi, M. Yamada, S. Tabata, DNA Res. 2002, 9, 123-130.

[17] a) J. A. Campbell, G. J. Davies, V. Bulone, B. Henrissat, Biochem. J. 1997, 326 (Pt 3), 929-939; b) P. M. Coutinho, E. Deleury, G. J. Davies, B. Henrissat, J. Mol. Biol. 2003, 328, 307-317.

[18] H. van Der Wel, H. R. Morris, M. Panico, T. Paxton, S. J. North, A. Dell, J. M. Thomson, C. M. West, J. Biol. Chem. 2001, 276, 33952-33963.

[19] S. W. Lin, T. M. Yuan, J. R. Li, C. H. Lin, Biochemistry 2006, 45, 8108-8116.

[20] H. Y. Sun, S. W. Lin, T. P. Ko, J. F. Pan, C. L. Liu, C. N. Lin, A. H. Wang, C. H. Lin, J. Biol. Chem. 2007, 282, 9973-9982.

[21] a) W. Wang, T. Hu, P. A. Frantom, T. Zheng, B. Gerwe, D. S. Del Amo, S. Garret, R. D. Seidel, 3rd, P. Wu, Proc. Natl. Acad. Sci. U.S.A 2009, 106, 16096-16101; b) H. Yu, K. Lau, Y. Li, G. Sugiarto, X. Chen, Curr. Protoc. Chem. Biol. 2012, 4, 233-247; c) G. Sugiarto, K. Lau, J. Qu, Y. Li, S. Lim, S. Mu, J. B. Ames, A. J. Fisher, X. Chen, ACS Chem. Biol. 2012, 7, 1232-1240; d) G. Sugiarto, K. Lau, H. Yu, S. Vuong, V. Thon, Y. Li, S. Huang, X. Chen, Glycobiology 2011, 21, 387-396.

[22] a) S. Hakomori, Biochim. Biophys. Acta 1999, 1473, 247-266; b) J. A. Letts, N. L. Rose, Y. R. Fang, C. H. Barry, S. N. Borisova, N. O. Seto, M. M. Palcic, S. V. Evans, J. Biol. Chem. 2006, 281, 3625-3632.

[23] L. Zhang, K. Lau, J. Cheng, H. Yu, Y. Li, G. Sugiarto, S. Huang, L. Ding, V. Thon, P. G. Wang, X. Chen, Glycobiology 2010, 20, 1077-1088.

[24] W. Yi, X. Liu, Y. Li, J. Li, C. Xia, G. Zhou, W. Zhang, W. Zhao, X. Chen, P. G. Wang, Proc. Natl. Acad. Sci. U.S.A 2009, 106, 4207-4212.

[25] K. Lau, V. Thon, H. Yu, L. Ding, Y. Chen, M. M. Muthana, D. Wong, R. Huang, X. Chen, Chem. Commun. 2010, 46, 6066-6068.

[26] R. Kuhn, H. H. Baer, A. Gauhe, Chem. Ber. 1956, 89, 2514-2523.

[27] a) D. L. Aldredge, M. R. Geronimo, S. Hua, C. C. Nwosu, C. B. Lebrilla, D. Barile, Glycobiology 2013, 23, 664-676; b) N. Tao, E. J. DePeters, S. Freeman, J. B. German, R. Grimm, C. B. Lebrilla, J. Dairy Sci. 2008, 91, 3768-3778.

[28] N. Tao, K. L. Ochonicky, J. B. German, S. M. Donovan, C. B. Lebrilla, J. Agric. Food Chem. 2010, 58, 4653-4659.

[29] Y. Hsu, X. A. Lu, M. M. Zulueta, C. M. Tsai, K. I. Lin, S. C. Hung, C. H. Wong, J. Am. Chem. Soc. 2012, 134, 4549-4552.

[30] T. Miyazaki, T. Sato, K. Furukawa, K. Ajisaka, Methods Enzymol. 2010, 480, 511-524.

[31] R. G. LoCascio, M. R. Ninonuevo, S. L. Freeman, D. A. Sela, R. Grimm, C. B. Lebrilla, D. A. Mills, J. B. German, J. Agric. Food Chem. 2007, 55, 8914-8919.

[32] M. A. Underwood, K. M. Kalanetra, N. A. Bokulich, Z. T. Lewis, M. Mirmiran, D. J. Tancredi, D. A. Mills, J. Pediatr. 2013, 163, 1585-1591 e1589.

[33] a) Z. T. Lewis, S. M. Totten, J. T. Smilowitz, M. Popovic, E. Parker, D. G. Lemay, M. L. Van Tassell, M. J. Miller, Y. S. Jin, J. B. German, C. B. Lebrilla, D. A. Mills, Microbiome 2015, 3, 13; b) M. N. Huda, Z. Lewis, K. M. Kalanetra, M. Rashid, S. M. Ahmad, R. Raqib, F. Qadri, M. A. Underwood, D. A. Mills, C. B. Stephensen, Pediatrics 2014, 134, e362-372.

[34] H. Yu, V. Thon, K. Lau, L. Cai, Y. Chen, S. Mu, Y. Li, P. G. Wang and X. Chen, Chem. Commun., 2010, 46, 7507-7509.

[35] S. Ruiz-Moyano, S. M. Totten, D. A. Garrido, J. T. Smilowitz, J. B. German, C. B. Lebrilla and D. A. Mills, Appl. Environ. Microbiol., 2013, 79, 6040-6049.

What is claimed is:

1. A reaction mixture comprising:

an α1-2-fucosyltransferase enzyme having at least 90% sequence identity to SEQ ID NO:1 (Te2FT), wherein the α1-2-fucosyltransferase enzyme comprises the sequences of GGLGNQMFQYA (SEQ ID NO:16), SLHIRRGDY (SEQ ID NO:17), VFSDDPQW (SEQ ID NO:18), and DMQLMSACRHHIIANSTFSWW-GAWLNPRPDKVVIAPRHWF (SEQ ID NO:19);

a bifunctional L-fucokinase/GDP-fucose pyrophosphorylase enzyme (FKP) having at least 90% sequence identity to SEQ ID NO:2;

a fucose donor comprising a nucleotide and a fucosyl moiety, and a β1-3-galactoside acceptor, wherein the acceptor comprises an oligosaccharide or a polysaccharide; and wherein the reaction mixture produces an α1-2-fucosylated β1-3 linked galactoside comprising the oligosaccharide or polysaccharide.

2. The mixture of claim 1, wherein the fucose donor is guanidine 5'-diphosphate-fucose (GDP-fucose).

3. The reaction mixture of claim 1, wherein the β1-3-galactoside acceptor is Galβ1-3GlcNAcβ2AA.

4. The reaction mixture of claim 1, wherein the β1-3-galactoside acceptor is Galβ1-3GlcNAcβOR, Galβ1-3GlcNAcαOR, Galβ1-3GalNAcαOR, or Galβ1-3GalNAcβOR, and wherein R is a monosaccharide or an oligosaccharide.

5. The reaction mixture of claim 1, wherein the β1-3-galactoside acceptor is Galβ1-3GalNAcαProN$_3$, Galβ1-3GalNAcβProN$_3$, Galβ1-3GlcNAcαProN$_3$, Galβ1-3GlcNAcβProN$_3$ or lacto-N-tetraose.

6. A method of making an α1-2-fucosylated β1-3 linked galactoside, the method comprising incubating a reaction mixture comprising:

an α1-2-fucosyltransferase enzyme having at least 90% sequence identity to SEQ ID NO:1 (Te2FT), wherein the α1-2-fucosyltransferase enzyme comprises the sequences of GGLGNQMFQYA (SEQ ID NO:16), SLHIRRGDY (SEQ ID NO:17), VFSDDPQW (SEQ ID NO:18), and DMQLMSACRHHIIANSTFSWW-GAWLNPRPDKVVIAPRHWF (SEQ ID NO:19);

a bifunctional L-fucokinase/GDP-fucose pyrophosphorylase enzyme (FKP) having at least 90% sequence identity to SEQ ID NO:2;

a fucose donor comprising a nucleotide and a fucosyl moiety; and a β1-3-galactoside acceptor, under conditions suitable to form the α1-2-fucosylated β1-3 linked galactoside.

7. The method of claim 6, wherein the β1-3-galactoside acceptor is selected from the group consisting of Galβ1-3GlcNAcβProN$_3$, Galβ1-3GlcNAcαProN$_3$, Galβ1-3GalNAcβProN$_3$, and Galβ1-3GalNAcαProN$_3$.

8. The method of claim 6, wherein the β1-3-galactoside acceptor is lacto-N-tetraose.

9. The method of claim 6, wherein the α1-2-fucosylated β1-3 linked galactoside is a human blood group H antigen or lacto-N-fucopentaose I.

10. The method of claim 6, wherein the reaction mixture further comprises an inorganic pyrophosphatase enzyme (PpA) having at least 90% sequence identity to SEQ ID NO:3.

11. The method of claim 6, wherein the α1-2-fucosylated β1-3 linked galactoside is selected from the group consisting of Fucα1-2Galβ1-3GlcNAcβProN$_3$, Fucα1-2Galβ1-3GlcNAcαProN$_3$, Fucα1-2Galβ1-3GalNAcβProN$_3$, and Fucα1-2Galβ1-3GalNAcαProN$_3$.

12. The method of claim 6, wherein the α1-2-fucosylated β1-3 linked galactoside is lacto-N-fucopentaose I.

13. The reaction mixture of claim 1, wherein the α1-2-fucosyltransferase enzyme has 100% sequence identity to SEQ ID NO:1.

14. The reaction mixture of claim 1, wherein the reaction mixture further comprises an inorganic pyrophosphatase enzyme (PpA) having at least 90% sequence identity to SEQ ID NO:3.

15. The reaction mixture of claim 14, wherein the α1-2-fucosyltransferase enzyme has at least 95% sequence identity to SEQ ID NO:1, the FKP has at least 95% sequence identity to SEQ ID NO:2 and the PpA has at least 95% sequence identity to SEQ ID NO:3.

16. The reaction mixture of claim 14, wherein the FKP has 100% sequence identity to SEQ ID NO:2 and the PpA has 100% sequence identity to SEQ ID NO:3.

17. The reaction mixture of claim 14, wherein the α1-2-fucosyltransferase enzyme has 100% sequence identity to SEQ ID NO:1, the FKP has 100% sequence identity to SEQ ID NO:2, and the PpA has 100% sequence identity to SEQ ID NO:3.

18. The method of claim 10, wherein the PpA has at least 95% sequence identity to SEQ ID NO:3.

19. The method of claim 18, wherein the α1-2-fucosyltransferase enzyme has at least 95% sequence identity to SEQ ID NO:1 and the FKP has at least 95% sequence identity to SEQ ID NO:2.

20. The method of claim 10, wherein the FKP has 100% sequence identity to SEQ ID NO:2 and the PpA has 100% sequence identity to SEQ ID NO:3.

21. The method of claim 6, wherein the fucose donor is guanidine 5'-diphosphate-fucose (GDP-fucose).

* * * * *